(12) United States Patent
Tanaka et al.

(10) Patent No.: US 9,951,163 B2
(45) Date of Patent: Apr. 24, 2018

(54) (METH)ACRYLATE COMPOUND, (METH)ACRYLIC COPOLYMER AND PHOTOSENSITIVE RESIN COMPOSITION CONTAINING SAME

(71) Applicant: Mitsubishi Gas Chemical Company, Inc., Tokyo (JP)

(72) Inventors: Hiroyasu Tanaka, Tokyo (JP); Shoichi Hayakawa, Mie (JP); Hiroyuki Tanagi, Tokyo (JP); Kikuo Furukawa, Tokyo (JP); Hiroshi Horikoshi, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 15/114,711

(22) PCT Filed: Jan. 30, 2015

(86) PCT No.: PCT/JP2015/052742
§ 371 (c)(1),
(2) Date: Jul. 27, 2016

(87) PCT Pub. No.: WO2015/115613
PCT Pub. Date: Aug. 6, 2015

(65) Prior Publication Data
US 2016/0347896 A1 Dec. 1, 2016

(30) Foreign Application Priority Data

Jan. 31, 2014 (JP) .................................. 2014-016875
Jan. 31, 2014 (JP) .................................. 2014-016877

(51) Int. Cl.
*G03F 7/004* (2006.01)
*C08F 220/28* (2006.01)
(Continued)

(52) U.S. Cl.
CPC ............ *C08F 220/28* (2013.01); *C07C 67/28* (2013.01); *C07C 69/75* (2013.01); *C07D 307/33* (2013.01);
(Continued)

(58) Field of Classification Search
CPC ....... C07C 67/28; G03F 7/039; G03F 7/0397; G03F 7/004; C08F 220/28; C08F 220/283; C08F 220/2832
(Continued)

(56) References Cited
U.S. PATENT DOCUMENTS 4,258,204 A * 3/1981 Banks ...................... C07C 67/14
560/205
4,435,594 A * 3/1984 Matsumura ............. C07C 67/08
560/205
(Continued)

FOREIGN PATENT DOCUMENTS

JP  H04-039665 A  2/1992
JP  H10-319595 A  12/1998
(Continued)

OTHER PUBLICATIONS

Machine translation of JP 2016-0955-7 (no date).*
(Continued)

*Primary Examiner* — Amanda C Walke
(74) *Attorney, Agent, or Firm* — Fitch, Even, Tabin & Flannery LLP

(57) ABSTRACT

The present invention provides a resist or a compound for use as a resist, which is highly sensitive and well-balanced without losing the fundamental physical properties required as a chemically amplified resist (e.g., resolution, line edge roughness (LER)).

The present invention is directed to a (meth)acrylate compound represented by general formula (1) and a process for preparation thereof, as well as a (meth)acrylic copolymer obtainable by polymerization of the (meth)acrylate compound of general formula (1) and a photosensitive resin composition thereof:

[Formula 1]

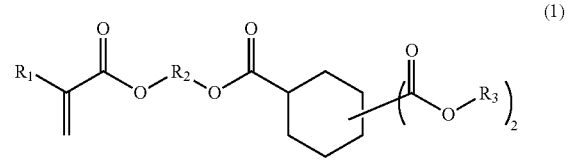

(1)

(wherein $R_1$ represents a hydrogen atom or a methyl group, $R_2$ represents a linear or branched alkyl group containing 2 to 4 carbon atoms, and each $R_3$ may be the same or different and represents a group represented by the following formula (2) or (3), etc.)

[Formula 2]

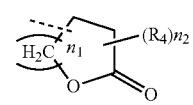

(2)

[Formula 3]

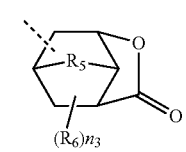

(3)

(provided that formulae (2) and (3) are as defined in the specification of the present application).

20 Claims, No Drawings

(51) Int. Cl.
*C07C 67/28* (2006.01)
*C07D 307/33* (2006.01)
*G03F 7/039* (2006.01)
*C07D 307/93* (2006.01)
*C07C 69/75* (2006.01)
*C08F 120/28* (2006.01)

(52) U.S. Cl.
CPC .......... *C07D 307/93* (2013.01); *C08F 120/28* (2013.01); *G03F 7/039* (2013.01); *G03F 7/0397* (2013.01); *C07C 2601/14* (2017.05); *C08F 2220/283* (2013.01)

(58) Field of Classification Search
USPC .................. 430/270.1, 913; 526/281, 317.1; 524/558, 559
See application file for complete search history.

(56) References Cited

U.S. PATENT DOCUMENTS

| | | | |
|---|---|---|---|
| 6,517,994 B2 * | 2/2003 | Watanabe | C07D 307/00 430/270.1 |
| 6,656,659 B1 | 12/2003 | Nozaki et al. | |
| 8,765,354 B2 * | 7/2014 | Utsumi | G03F 7/0045 430/270.1 |
| 8,822,129 B2 * | 9/2014 | Iwato | G03F 7/0392 430/270.1 |
| 8,841,060 B2 * | 9/2014 | Kataoka | G03F 7/0045 430/270.1 |
| 8,865,389 B2 * | 10/2014 | Hirano | G03F 7/0045 430/270.1 |
| 9,040,222 B2 * | 5/2015 | Suka | G03F 7/039 430/270.1 |
| 9,081,277 B2 * | 7/2015 | Matsuda | C07C 381/12 |
| 9,122,152 B2 * | 9/2015 | Hatakeyama | G03F 7/004 |
| 9,182,668 B2 * | 11/2015 | Hasegawa | G03F 7/038 |
| 9,291,898 B2 * | 3/2016 | Yokokawa | G03F 7/0002 |
| 9,323,158 B2 * | 4/2016 | Li | G02B 17/0657 |
| 9,366,958 B2 * | 6/2016 | Ohashi | G03F 7/027 |
| 9,448,482 B2 * | 9/2016 | Iwato | G03F 7/40 |
| 9,523,912 B2 * | 12/2016 | Kataoka | G03F 7/038 |
| 9,527,809 B2 * | 12/2016 | Yokokawa | G03F 7/039 |
| 2004/0058270 A1 | 3/2004 | Iwai et al. | |
| 2009/0111961 A1 * | 4/2009 | Kubo | C08F 220/28 526/266 |
| 2010/0048848 A1 * | 2/2010 | Yamagishi | C08F 2/00 526/266 |
| 2011/0045405 A1 * | 2/2011 | Lee | C07D 307/93 430/270.1 |
| 2011/0046333 A1 * | 2/2011 | Kubo | C08F 220/28 526/266 |
| 2012/0273924 A1 * | 11/2012 | Matsuda | C07C 381/12 257/632 |
| 2013/0052568 A1 | 2/2013 | Tsuchihashi et al. | |
| 2016/0052859 A1 * | 2/2016 | Ochiai | C08F 122/18 430/270.1 |

FOREIGN PATENT DOCUMENTS

| | | |
|---|---|---|
| JP | 2000-026446 A | 1/2000 |
| JP | 2003-089676 A | 3/2003 |
| JP | 2003-167346 A | 6/2003 |
| JP | 2004-323704 A | 11/2004 |
| JP | 2005-154304 A | 6/2005 |
| JP | 2006-243474 A | 9/2006 |
| JP | 2010-039142 A | 2/2010 |
| JP | 2013-044809 A | 3/2013 |
| JP | 2016095507 A * | 5/2016 |

OTHER PUBLICATIONS

International Search Report dated Mar. 3, 2015 for PCT/JP2015/052742 and English translation of the same (5 pages).

Sato et al. "Thermal Latent Polyhydric Carboxylic Acid Derivatives and Their Application to Network Polymer (I)," Network Polymer vol. 19, No. 4, 1998, pp. 215-222; English Synopsis submitted herewith (7 Pages).

* cited by examiner

(METH)ACRYLATE COMPOUND, (METH)ACRYLIC COPOLYMER AND PHOTOSENSITIVE RESIN COMPOSITION CONTAINING SAME

CROSS-REFERENCE TO RELATED APPLICATIONS

This application is a U.S. national phase application filed under 35 U.S.C. § 371 of International Application PCT/JP2015/052742, filed Jan. 30, 2015, designating the United States, which claims priority from Japanese Application Numbers 2014-016875 and 2014-016877, each filed Jan. 31, 2014, which are hereby incorporated herein by reference in their entirety.

TECHNICAL FIELD

The present invention relates to novel (meth)acrylate compounds including acid-dissociable ester compounds, which are suitable for use as starting materials or the like for resists for KrF, ArF and F2 excimer lasers or chemically amplified resists for X-rays, electron beams or EUV (extreme ultraviolet rays), and also relates to (meth)acrylic copolymers and photosensitive resin compositions comprising the same.

BACKGROUND ART

In response to the increasing capacity of flash memory, a type of storage device, and to expansion of the market for image sensors or the like designed for high-resolution cameras in mobile phones and smartphones, there arises a strong demand for further micropatterning in semiconductor devices. In the manufacture of these various electronic devices, photolithographic techniques are used widely. In photolithography, efforts have been made to facilitate micropatterning by using a light source of shorter wavelength. When a KrF excimer laser or a short wavelength light source developed thereafter is used as a light source, chemically amplified resists are used in most cases and they are generally configured in the form of solutions containing a functional resin serving as a base material and a photoacid generator and further containing several types of additives. Among these components, a functional resin serving as a base material is a determinant of resist performance and it is important for such a functional resin to have a good balance of various properties including etching resistance, substrate adhesion, transparency against a light source to be used, development speed, etc.

Functional resins for use in photoresists for KrF excimer lasers are usually polymers comprising, e.g., a vinyl compound or acrylate as a repeating unit. For example, hydroxystyrenic resins have been proposed in the case of resists for KrF excimer laser lithography (Patent Document 1), while acrylic resins whose backbone is composed of adamantyl (meth)acrylate have been proposed in the case of resists for ArF excimer laser lithography (Patent Documents 2 to 6); and hence the required backbone is now being fixed. However, polymers composed of a single type of repeating unit are not used for this purpose. This is because a single type of repeating unit cannot satisfy all of the properties including etching resistance. In actual cases, several types, i.e., two or more types of repeating units having functional groups required to improve the individual properties are used for copolymerization to give a functional resin, and the resulting functional resin is further blended with a photoacid generator and others and dissolved in a solvent for use as a photosensitive resin composition. Moreover, heat-curable compositions known for use as photoresists or the like include those comprising hemiacetal ester derivatives (Patent Documents 7 and 8). However, since photoresists are generally heated at around 100° C. to 150° C. after pattern exposure (post-exposure bake), there is a concern that the hemiacetal skeleton will be thermally decomposed at 100° C. or higher temperatures (Patent Document 9 and Non-patent Document 1).

Recent lithographic processes have further facilitated micropatterning. ArF excimer laser lithography has continued to progress from liquid immersion exposure to double patterning exposure, while various efforts have also been made to develop extreme ultraviolet (EUV)-based lithography, which receives attention as a next-generation lithographic technique, as well as direct writing with electron beams and negative tone development. Under these circumstances, there is a demand for the development of a new functional monomer suitable for micropatterning.

PRIOR ART DOCUMENTS

Patent Documents

Patent Document 1: JP 2006-243474 A
Patent Document 2: JP H4-39665 A
Patent Document 3: JP H10-319595 A
Patent Document 4: JP 2000-26446 A
Patent Document 5: JP 2003-167346 A
Patent Document 6: JP 2004-323704 A
Patent Document 7: JP 2005-154304 A
Patent Document 8: JP 2003-89676 A
Patent Document 9: JP 2013-44809 A

Non-Patent Documents

Non-patent Document 1: Network Polymer Vol. 19, No. 4, 1998, pages 215-221

SUMMARY OF THE INVENTION

Under these circumstances, the present invention aims to provide, as a chemically amplified resist responsive to KrF excimer lasers, ArF excimer lasers, F2 excimer lasers, X-rays, electron beams or EUV, a novel functional monomer useful in the field of photolithography, e.g., a novel functional monomer having an acid-dissociable site, and a photosensitive resin composition comprising the same.

As a result of extensive and intensive efforts made to solve each of the problems stated above, the inventors of the present invention have found that a (meth)acrylate compound having a specific structure, particularly a methacrylic acid ester compound protected with an acid-degradable substituent(s) is a useful compound allowing pattern formation in lithographic operations conducted with KrF excimer lasers, ArF excimer lasers, F2 excimer lasers, X-rays, electron beams or EUV (extreme ultraviolet rays), etc. This finding led to the completion of the present invention.

Namely, the present invention relates to a (meth)acrylate compound represented by general formula (1) and a process for preparation thereof, as well as a (meth)acrylic copolymer composed of a (meth)acrylate compound represented by general formula (1) and a photosensitive resin composition thereof.

More specifically, the present invention is as follows.

(I) A (meth)acrylate compound represented by the following general formula (1):

[Formula 1]

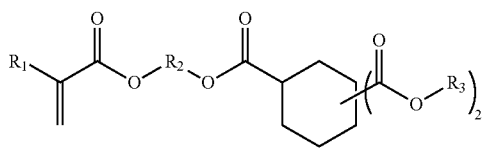
(1)

(wherein $R_1$ represents a hydrogen atom or a methyl group, $R_2$ represents a linear or branched alkylene group containing 2 to 4 carbon atoms, and each $R_3$ may be the same or different and represents a group represented by the following formula (2), (3), (20) or (30)).

It should be noted that if the number of carbon atoms in $R_2$ is in the range of 2 to 4, it is preferred because the glass transition temperature of the (meth)acrylate compound of formula (1) (or a polymer comprising the same) can be increased.

[Formula 2]

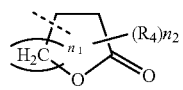
(2)

(wherein each $R_4$ may be the same or different and independently represents a methyl group, an ethyl group, a hydroxyl group or a halogen group, $n_1$ represents 1 to 4, and $n_2$ represents 0 to 2).

[Formula 3]

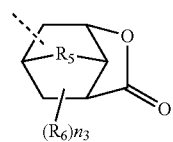
(3)

(wherein $R_5$ may be either present or absent and if present, it represents methylene (—$CH_2$—) or oxa (—O—), if there are two or more $R_6$, each may be the same or different and independently represents a hydroxyl group, a halogen group, a nitrile group, a carboxylic acid group, an alkyl carboxylate group containing 1 to 4 carbon atoms or an alkoxide group containing 1 to 4 carbon atoms, and $n_3$ represents 0 to 2).

[Formula 4]

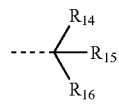
(20)

(wherein $R_{14}$, $R_{15}$ and $R_{16}$, which may be the same or different, each independently represent a cyclic, linear or branched alkyl group containing 1 to 13 carbon atoms, or $R_{15}$ and $R_{16}$ may be joined together to form a ring structure).

[Formula 5]

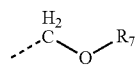
(30)

(wherein $R_7$ represents a cyclic, linear or branched alkyl group containing 1 to 10 carbon atoms or an oxygen-containing cyclic, linear or branched alkyl group containing 1 to 10 carbon atoms).

In the specification of the present application, it should be noted that the broken lines shown in the chemical formulae each represent a bond between a site including the broken line and another site.

(II) A process for preparation of the (meth)acrylate compound of general formula (1) according to (I) above wherein $R_3$ is represented by general formula (2) or (3), which comprises reacting an acid anhydride represented by general formula (4) with a (meth)acrylate derivative having a hydroxyl group represented by general formula (5) in the presence of an organic base to generate a (meth)acrylate derivative having a dicarboxylic acid group represented by general formula (6) and then allowing the (meth)acrylate derivative of general formula (6) to be directly provided, without being isolated, for reaction with a lactone compound represented by general formula (7) and/or (8):

[Formula 6]

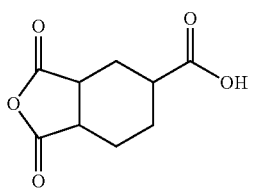
(4)

[Formula 7]

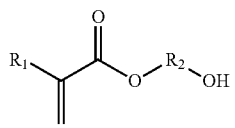
(5)

(wherein $R_1$ and $R_2$ are as defined in general formula (1))

[Formula 8]

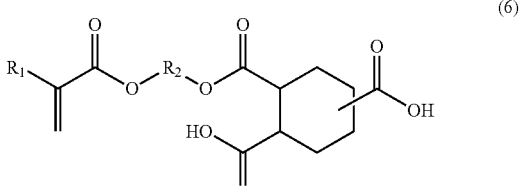
(6)

(wherein $R_1$ and $R_2$ are as defined in general formula (1))

[Formula 9]

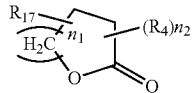
(7)

(wherein $R_4$, $n_1$ and $n_2$ are as defined in general formula (2), and $R_{17}$ is a halogen group)

[Formula 10]

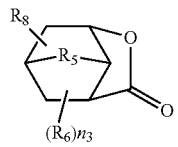
(8)

(wherein $R_5$, $R_6$ and $n_3$ are as defined in general formula (3), and $R_5$ is a halogen group).

(III) A process for preparation of the (meth)acrylate compound of general formula (1) according to (I) above wherein $R_3$ is represented by general formula (2) or (3), which comprises reacting the above (meth)acrylate derivative having a dicarboxylic acid group represented by general formula (6) with a lactone compound represented by general formula (9) and/or (10) in the presence of an acid catalyst:

[Formula 11]

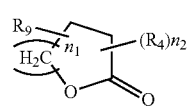
(9)

(wherein $R_4$, $n_1$ and $n_2$ are as defined in general formula (2), and $R_9$ is a hydroxyl group)

[Formula 12]

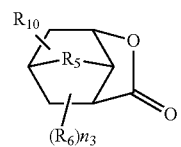
(10)

(wherein $R_5$, $R_6$ and $n_3$ are as defined in general formula (3), and $R_{10}$ is a hydroxyl group).

(IV) A (meth)acrylic copolymer comprising general formula (11) as a repeating unit, which is obtainable by polymerization of the (meth)acrylate compound according to (I) above:

[Formula 13]

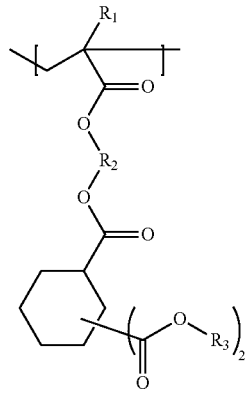
(11)

(wherein $R_1$ and $R_2$ are as defined in general formula (1) shown above, and $R_3$ is represented by general formula (2) or (3) shown above).

(V) The (meth)acrylic copolymer according to (IV) above, which further comprises at least one member selected from the following general formulae (12) to (14) as a repeating unit, in addition to the repeating unit of general formula (11) shown above:

[Formula 14]

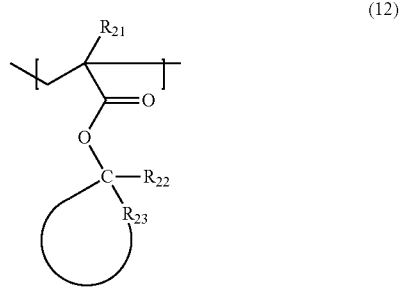
(12)

(wherein $R_{21}$ represents a hydrogen atom or a methyl group, $R_{22}$ represents an alkyl group containing 1 to 4 carbon atoms, and $R_{23}$ represents a cycloalkylene or cycloaliphatic alkylene group containing 5 to 20 carbon atoms)

[Formula 15]

(13)

(wherein $R_{31}$ represents a hydrogen atom or a methyl group, $R_{32}$ to $R_{33}$, which may be the same or different, each independently represent an alkyl group containing 1 to 4 carbon atoms, and $R_{34}$ represents an alkyl group containing 1 to 4 carbon atoms or a cycloalkyl or cycloaliphatic alkyl group containing 5 to 20 carbon atoms)

[Formula 16]

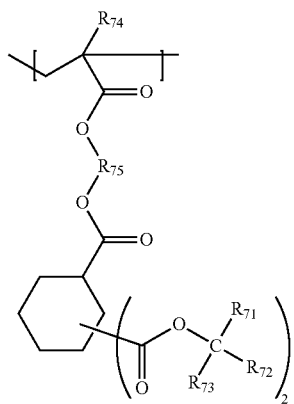

(14)

(wherein $R_{71}$ to $R_{73}$, which may be the same or different, each represent an alkyl group containing 1 to 4 carbon atoms or a cycloalkyl or cycloaliphatic alkyl group containing 5 to 20 carbon atoms, or $R_{72}$ and $R_{73}$ may be joined together to form a ring structure, $R_{74}$ represents a hydrogen atom or a methyl group, and $R_{75}$ represents a linear or branched alkylene group containing 2 to 4 carbon atoms).

(VI) A process for preparation of the (meth)acrylate compound of general formula (1) according to (I) above wherein $R_3$ is represented by general formula (20), which comprises reacting a (meth)acrylate derivative having a dicarboxylic acid group represented by general formula (21) or an acid halide thereof with a tertiary alcohol represented by general formula (22) or an alcoholate thereof:

[Formula 17]

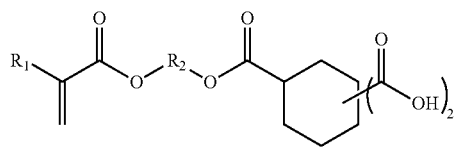

(21)

(wherein $R_1$ represents a hydrogen atom or a methyl group, and $R_2$ represents a linear or branched alkyl group containing 2 to 4 carbon atoms)

[Formula 18]

$$HO-\underset{R_{16}}{\overset{R_{14}}{\underset{|}{C}}}-R_{15}$$

(22)

(wherein $R_{14}$ to $R_{16}$ are as defined in general formula (20)).

(VII) A process for preparation of the (meth)acrylate compound of general formula (1) according to (I) above wherein $R_3$ is represented by general formula (30), which comprises reacting an acid anhydride represented by general formula (23) with a (meth)acrylate derivative having a hydroxyl group represented by general formula (24) in the presence of an organic base compound and then further reacting with a methyl ether compound represented by general formula (25):

[Formula 19]

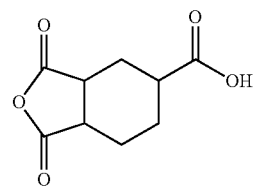

(23)

[Formula 20]

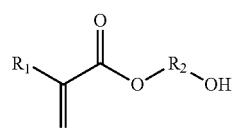

(24)

(wherein $R_1$ and $R_2$ are as defined in general formula (1))

[Formula 21]

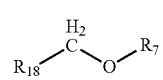

(25)

(wherein $R_7$ is as defined in general formula (30), and $R_{18}$ represents a halogen element).

(VIII) A (meth)acrylic copolymer comprising a repeating unit represented by general formula (26), which is obtainable by polymerization of the (meth)acrylate compound according to (I) above:

[Formula 22]

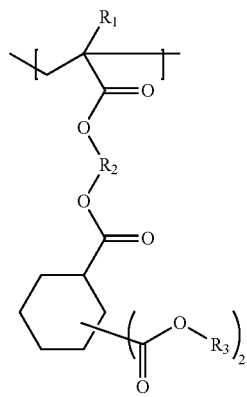

(26)

(wherein $R_1$ and $R_2$ are as defined in general formula (1) shown above, and $R_3$ is represented by general formula (20) or (30) shown above).

(IX) The (meth)acrylic copolymer according to (VIII) above, which further comprises at least one member selected from general formulae (27) to (28) as a repeating unit, in addition to the repeating unit of general formula (26):

[Formula 23]

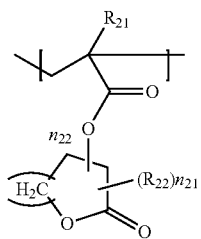

(27)

(wherein $R_{21}$ represents a hydrogen atom or a methyl group, $R_{22}$ represents a methyl group, an ethyl group, a hydroxyl group or a halogen group, $n_{21}$ represents 0 to 2, and $n_{22}$ represents 1 to 3)

[Formula 24]

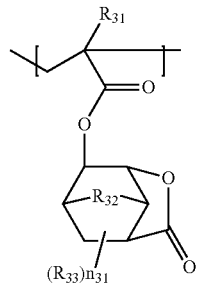

(28)

(wherein $R_{31}$ represents a hydrogen atom or a methyl group, $R_{32}$ represents methylene (—CH$_2$—) or oxa (—O—), each $R_{33}$ may be the same or different and independently represents a hydroxyl group, a halogen group, a nitrile group, a carboxylic acid group, an alkyl carboxylate group containing 1 to 4 carbon atoms or an alkoxide group containing 1 to 4 carbon atoms, and $n_{31}$ represents 0 to 2).

(X) A process for preparation of the (meth)acrylate compound according to (I) above wherein $R_3$ is represented by general formula (2) or (3) and is represented by general formula (20), which comprises reacting a (meth)acrylate derivative having a dicarboxylic acid group represented by general formula (21) or an acid halide thereof with a tertiary alcohol represented by general formula (22) or an alcoholate thereof and then further reacting with a lactone compound represented by general formula (9) and/or (10):

[Formula 25]

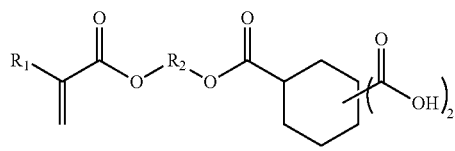

(21)

(wherein $R_1$ represents a hydrogen atom or a methyl group, and $R_2$ represents a linear or branched alkyl group containing 2 to 4 carbon atoms)

[Formula 26]

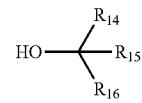

(22)

(wherein $R_{14}$ to $R_{16}$ are as defined in general formula (20))

[Formula 27]

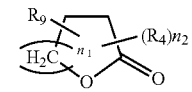

(9)

(wherein $R_4$, $n_1$ and $n_2$ are as defined in general formula (2), and $R_9$ is a hydroxyl group)

[Formula 28]

(10)

(wherein $R_5$, $R_6$ and $n_3$ are as defined in general formula (3), and $R_{10}$ is a hydroxyl group).

It should be noted that the (meth)acrylate compound according to (I) above wherein $R_3$ is represented by general formula (2) or (3) and is represented by general formula (20) is intended to mean a (meth)acrylate compound in which one of two $R_3$ is represented by general formula (2) or (3) and the other is represented by general formula (20).

(XI) A (meth)acrylic copolymer comprising a repeating unit represented by general formula (29), which is obtainable by polymerization of the (meth)acrylate compound according to (I) above:

[Formula 29]

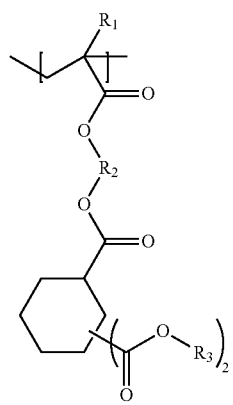

(29)

(wherein $R_1$ and $R_2$ are as defined in general formula (1) shown above, and $R_3$ is represented by general formula (2) or (3) shown above and is represented by general formula (20) shown above).

(XII) The (meth)acrylic copolymer according to (XI) above, which further comprises at least one member selected from general formula (31) as a repeating unit, in addition to the repeating unit of general formula (29):

[Formula 30]

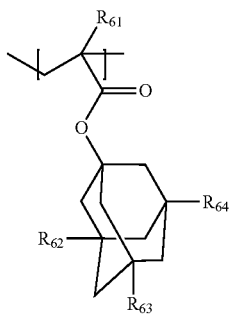

(31)

(wherein $R_{61}$ represents a hydrogen atom or a methyl group, $R_{62}$ to $R_{64}$, which may be the same or different, each independently represent a hydrogen atom, a hydroxyl group, a methyl group or an ethyl group).

(XIII) A photosensitive resin composition, which comprises the (meth)acrylic copolymer according to any one of (IV), (V), (VIII), (IX), (XI) and (XII) above and a photoacid generator.

The (meth)acrylate compounds of the present invention, particularly (meth)acrylate compounds having two lactone groups in one molecule can be expected to improve the solubility in a solvent, the adhesion to a substrate and the affinity to an alkaline developer, when compared to previously used monomers having one lactone group in one molecule. Improved affinity to an alkaline developer allows an improvement in sensitivity. Moreover, among the (meth)acrylate compounds of the present invention, those corresponding to acid-dissociable ester compounds (see (VI) to (IX) show above) will be deprotected to change their polarity by the action of an acid generated from a photoacid generator in lithographic operation, and thereby may be preferably used as positive resist materials or negative resist materials. In particular, because of having two deprotectable groups in one molecule, the above acid-dissociable ester compounds can be expected to improve the sensitivity, when compared to previously used acid-dissociable ester compounds having one deprotectable group in one molecule. If the sensitivity can be improved in this way, it is possible to lower the heating temperature in the heating step after exposure (i.e., the post-exposure bake step). Moreover, if the heating temperature can be lowered, it is possible to prevent the thermal diffusion of an acid generated upon exposure, which is advantageous to form a more fine pattern. In view of the foregoing, the (meth)acrylate compounds of the present invention including acid-dissociable ester compounds are preferred as derivatives suitable for micropatterning.

DESCRIPTION OF EMBODIMENTS

The present invention will be described in more detail below. The (meth)acrylate compounds of the present invention are represented by general formula (1).

More specifically, the (meth)acrylate compounds of the present invention may be exemplified as follows, but not limited thereto. Among them, preferred are compounds in which the carbon chain of $R_2$ is composed of 2 or 3 carbon atoms, more preferably 2 carbon atoms.

[Formula 31]

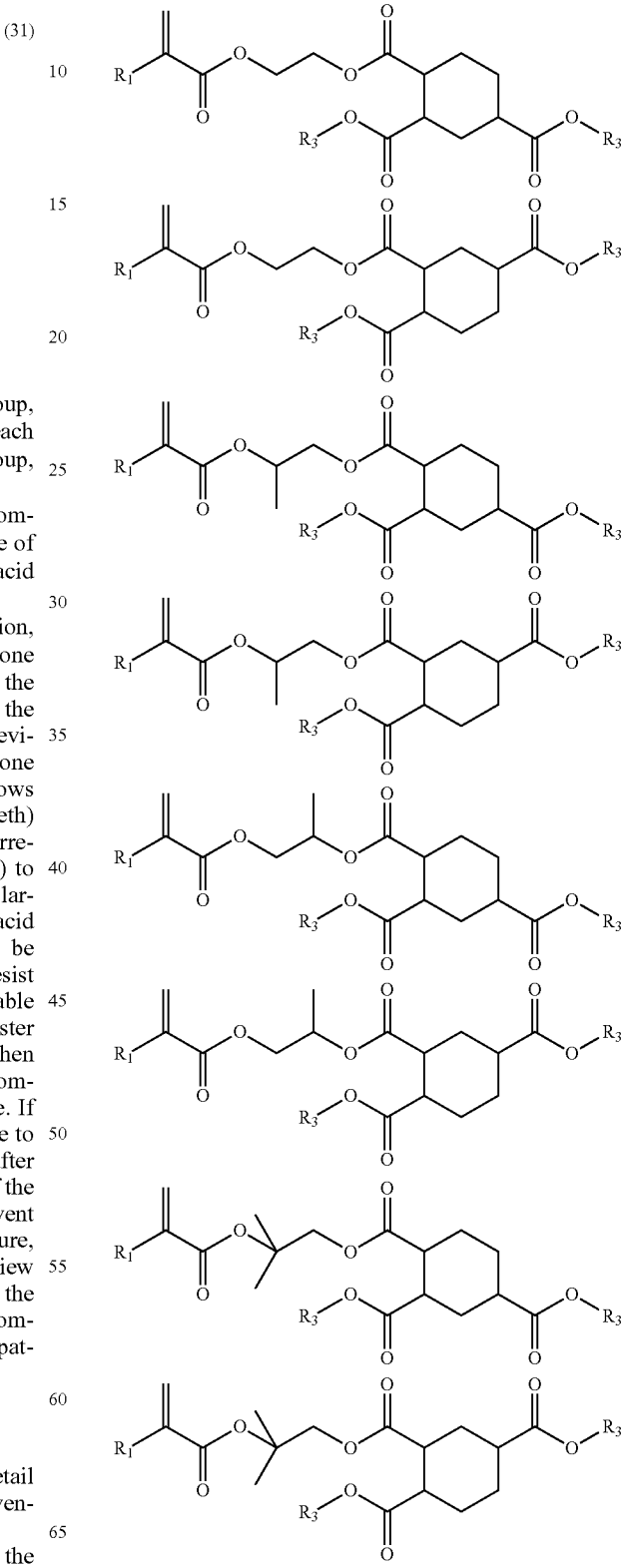

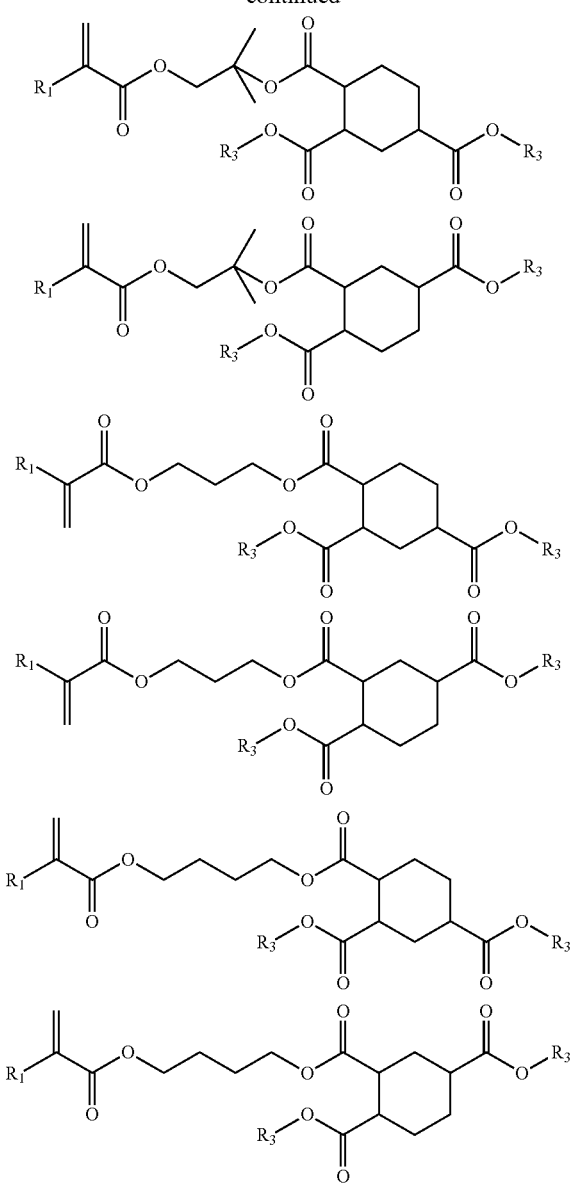
(wherein $R_1$ is a hydrogen atom or a methyl group, and $R_3$ may be exemplified as follows, but not limited thereto, provided that each $R_3$ may be the same or different)
[Formula 32]
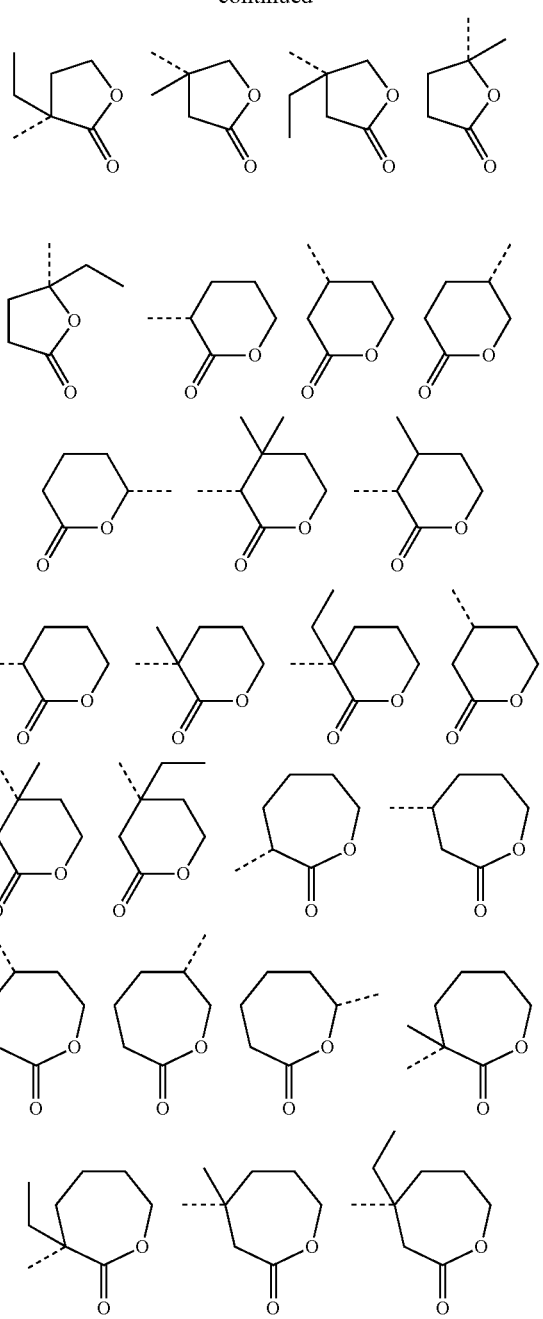
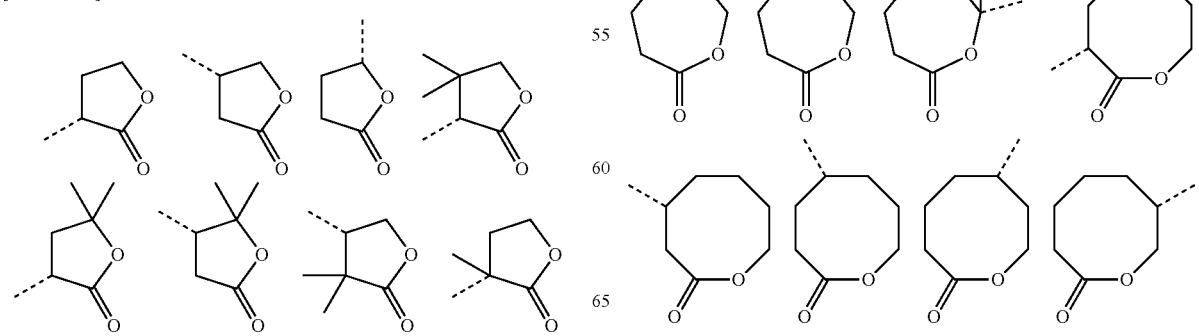

-continued

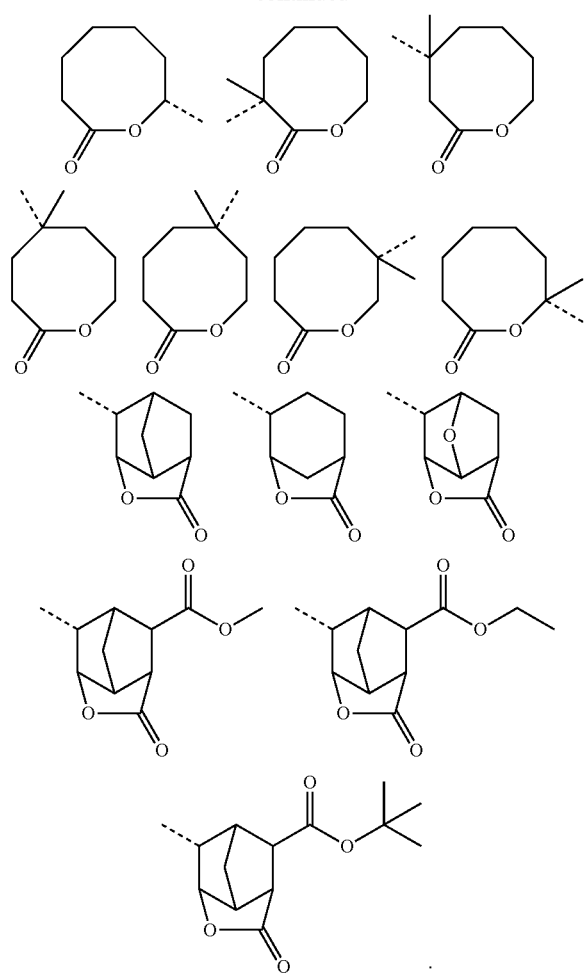

Among them, particularly preferred are the structures shown below.

[Formula 33]

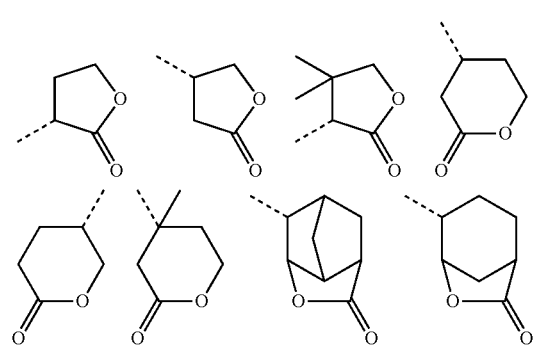

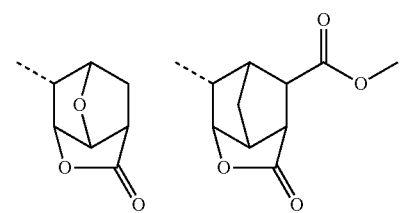

-continued

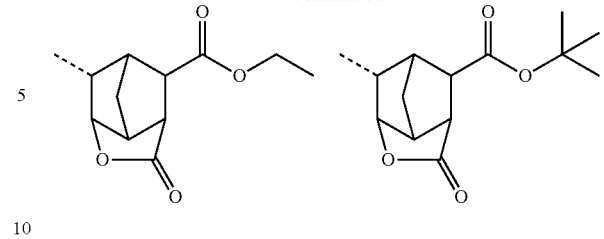

The (meth)acrylate compounds of the present invention represented by general formula (1) may be obtained, for example, by reacting an acid anhydride represented by general formula (4) with a (meth)acrylate derivative having a hydroxyl group represented by general formula (5) to give a (meth)acrylate derivative having a dicarboxylic acid group represented by general formula (6), and then further reacting with lactone compounds represented by general formulae (7) to (10). The above series of reactions may be conducted in sequence or may be conducted continuously in the same reaction vessel without collecting any intermediate reaction product.

[Formula 34]

(4)

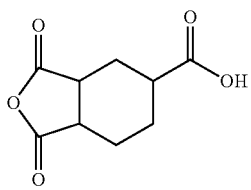

[Formula 35]

(5)

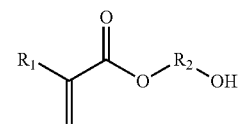

(wherein $R_1$ and $R_2$ are as defined in general formula (1))

[Formula 36]

(6)

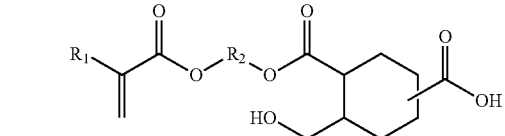

(wherein $R_1$ and $R_2$ are as defined in general formula (1))

[Formula 37]

(7)

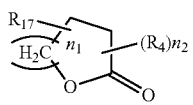

(wherein $R_4$, $n_1$ and $n_2$ are as defined in general formula (2), and $R_{17}$ is a halogen group)

[Formula 38]

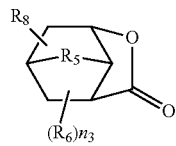

(8)

(wherein $R_5$, $R_6$ and $n_3$ are as defined in general formula (3), and $R_5$ is a halogen group)

[Formula 39]

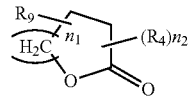

(9)

(wherein $R_4$, $n_1$ and $n_2$ are as defined in general formula (2), and $R_9$ is a hydroxyl group)

[Formula 40]

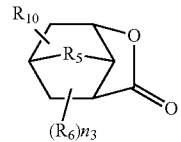

(10)

(wherein $R_5$, $R_6$ and $n_3$ are as defined in general formula (3), and $R_{10}$ is a hydroxyl group)

The (meth)acrylate derivative having a hydroxyl group represented by general formula (5) to be used in the present invention may be exemplified as follows.

[Formula 41]

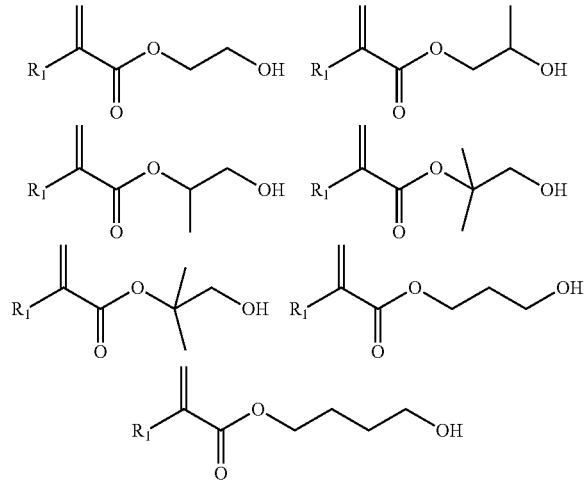

(wherein $R_1$ is as defined in general formula (1))

The (meth)acrylate derivative having a dicarboxylic acid group represented by general formula (6) to be used in the present invention may be exemplified as follows.

[Formula 42]

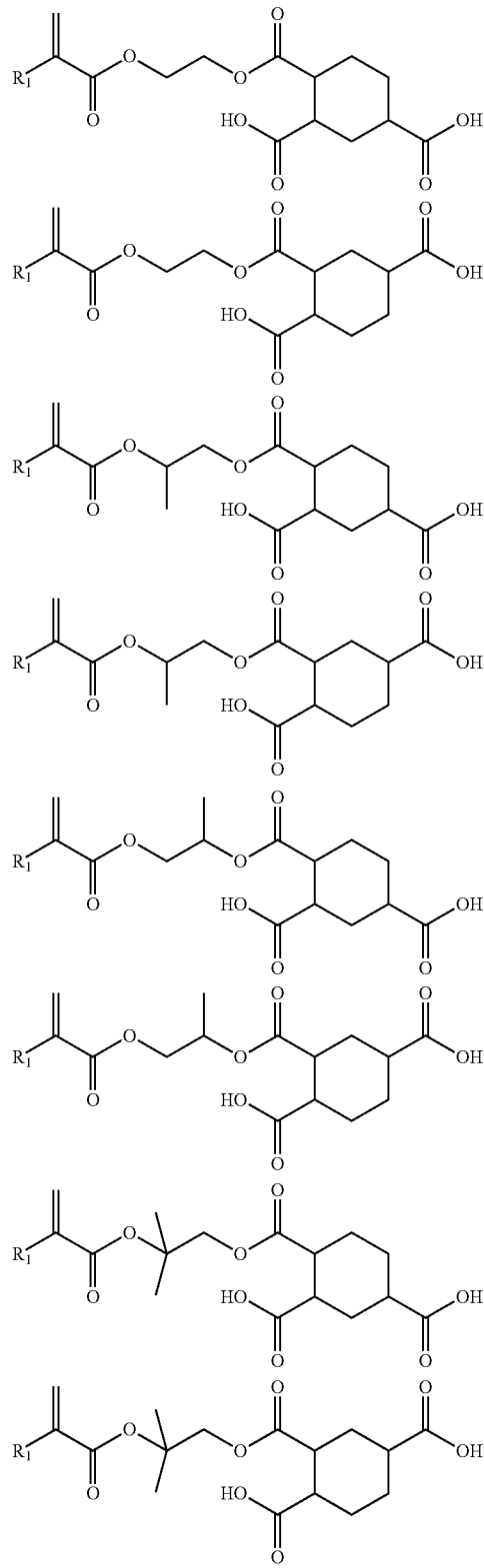

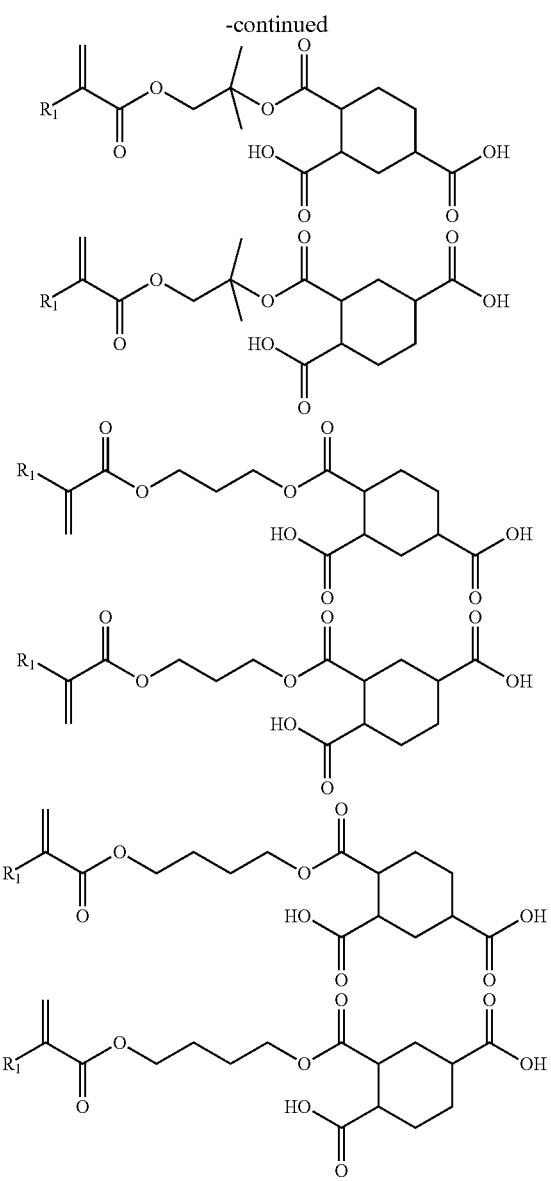
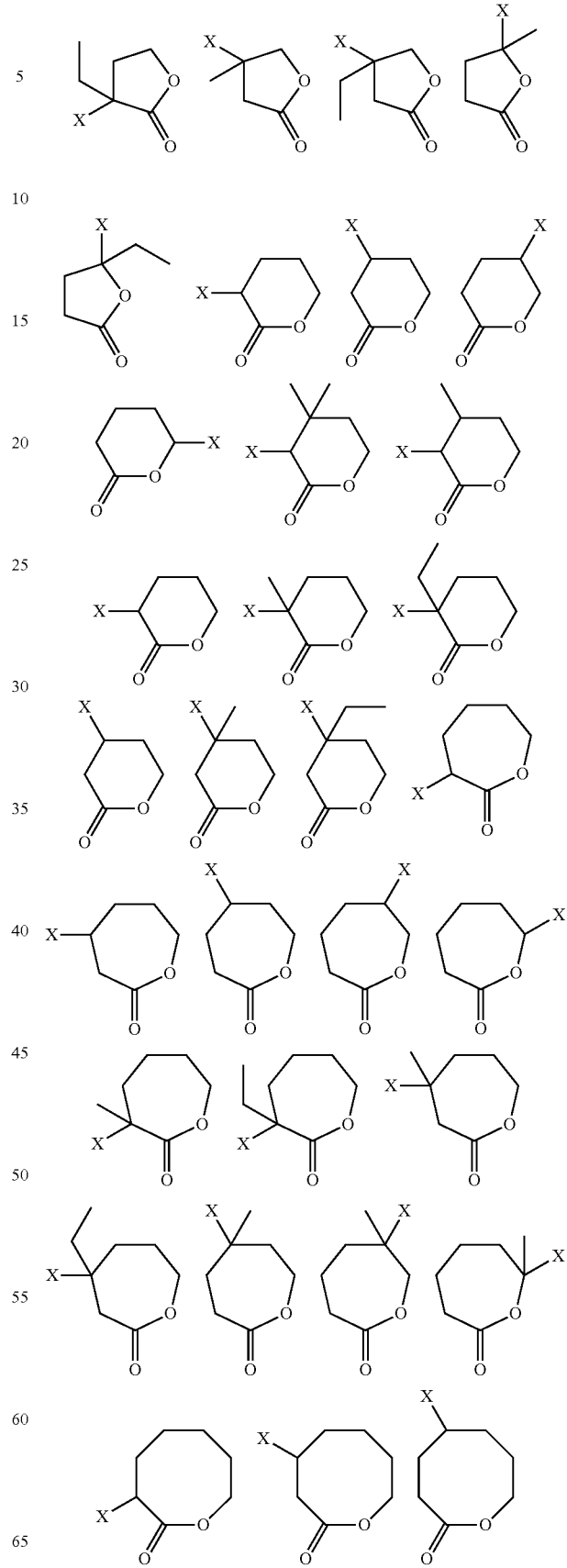
(wherein $R_1$ is as defined in general formula (1))
The lactone compounds represented by general formulae (7) to (10) to be used in the present invention may be exemplified as follows.
[Formula 43]
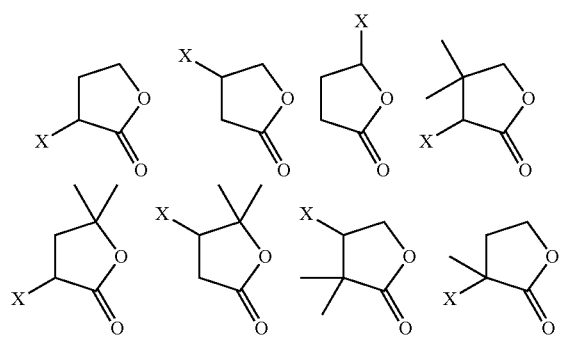

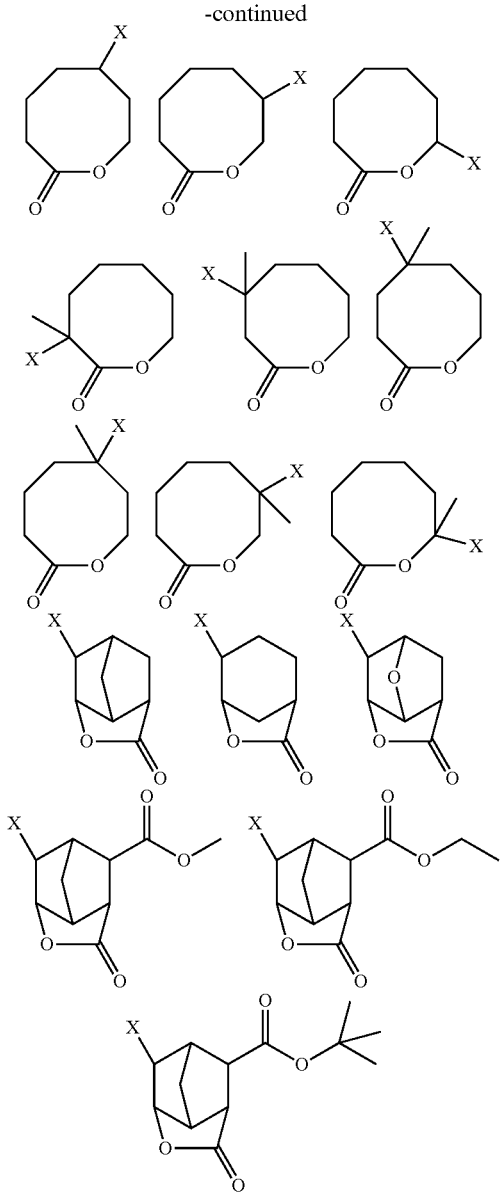

(wherein X is a halogen group or a hydroxyl group)

How to prepare the (meth)acrylate compounds of the present invention will be described in more detail. First, the (meth)acrylate derivative having a dicarboxylic acid group represented by general formula (6) is obtained from the acid anhydride represented by general formula (4) and the (meth)acrylate derivative having a hydroxyl group represented by general formula (5). The reaction in this case is a reaction in which 1 mole of acid anhydride is reacted with 1 mole of hydroxyl group to cause ring opening in the cyclic acid anhydride group to thereby generate 1 mole of carboxyl group. This ring-opening half ester reaction may be accomplished in a known manner, e.g., in the presence of an organic base compound added as a catalyst and in an organic solvent at a temperature ranging from −20° C. to 200° C., preferably from 0° C. to 100° C., more preferably from 0° C. to 50° C.

The (meth)acrylate derivative having a hydroxyl group represented by general formula (5) may be added in an amount of 0.5 to 5.0 equivalents, preferably 0.6 to 3.0 equivalents, more preferably 0.8 to 1.5 equivalents, relative to the acid anhydride represented by general formula (4). The amount within this range is also preferred in economical aspect because the reaction will proceed well and the desired product, i.e., the (meth)acrylate derivative having a dicarboxylic acid group represented by general formula (6) is obtained in high yield.

Examples of an organic base compound available for use as a catalyst include tertiary amines such as trimethylamine, triethylamine, tripropylamine, diisopropylethylamine, tributylamine, tripentylamine, and trihexylamine; aliphatic amines having an aromatic ring(s), such as N-methylaniline, N,N-dimethylaniline, phenyldimethylamine, diphenylmethylamine, and triphenylamine; cycloaliphatic amines such as pyrrolidine, 1-methylpyrrolidine, 2-methylpyrrolidine, 3-methylpyrrolidine, and proline; amidines such as 1,8-diazabicyclo[5.4.0]-7-undecene, and 1,5-diazabicyclo[4.3.0]-5-nonene; guanidines such as guanidine, 1,1,3,3-tetramethylguanidine, and 1,2,3-triphenylguanidine; pyridines such as pyridine, 2-methylpyridine, 3-methylpyridine, 4-methylpyridine, 2,6-dimethylpyridine, and N,N-dimethyl-5-aminopyridine; quaternary ammonium salts such as tetramethylammonium hydroxide, and tetraethylammonium hydroxide, etc. The above catalysts may be used either alone or as a mixture of two or more of them. The amount to be added is 0.0001 to 20 equivalents, preferably 0.001 to 10 equivalents, and more preferably 0.005 to 3 equivalents, relative to the total number of moles of the carboxyl group substituted on the acid anhydride represented by general formula (4) and the carboxyl group generated from the acid anhydride upon reaction.

In the reaction intended in the present invention to obtain the (meth)acrylate derivative having a dicarboxylic acid group represented by general formula (6) from the acid anhydride represented by general formula (4) and the (meth)acrylate derivative having a hydroxyl group represented by general formula (5), a solvent available for use may be exemplified by dimethyl sulfoxide, diethyl ether, diisopropyl ether, methyl-t-butyl ether, tetrahydrofuran, dioxane, dimethylacetamide, dimethylformamide, acetonitrile, benzene, toluene, xylene, mesitylene, pseudocumene, chloroform, chlorobenzene, dichloroethane, dichloromethane, acetone, methyl ethyl ketone, and methyl isobutyl ketone, although preparation is also possible in the absence of any solvent.

The acid anhydride represented by general formula (4), the (meth)acrylate derivative having a hydroxyl group represented by general formula (5) and the organic base compound(s) may be added in any order. However, it is preferred that the (meth)acrylate derivative having a hydroxyl group represented by general formula (5) and the organic base compound(s) are dissolved in a solvent to prepare a solution and the cycloaliphatic acid anhydride represented by general formula (4) is then added thereto, because fewer by-products are generated in this order. The acid anhydride may be dissolved in a solvent and added dropwise or may be added without any solvent.

The reaction temperature and reaction time actually used for the above reaction will vary depending on the substrate concentration and the type of catalyst(s) to be used, although the above reaction may generally be conducted at a reaction temperature of −20° C. to 150° C., preferably 0° C. to 100° C., for a reaction time of 1 hour to 24 hours, preferably 1 hour to 10 hours, and under normal, reduced or elevated pressure. Moreover, the reaction may be conducted in any known mode selected as appropriate from batch, semi-batch and continuous modes, etc.

The (meth)acrylate compounds represented by general formula (1) may be obtained by reacting the (meth)acrylate derivative having a dicarboxylic acid group represented by general formula (6) with the lactone compounds represented by general formulae (7) to (10). Alternatively, they may also be obtained by reacting the acid anhydride represented by general formula (4) with the (meth)acrylate derivative having a hydroxyl group represented by general formula (5), followed by reaction with the lactone compounds represented by general formulae (7) to (10) without isolating the (meth)acrylate derivative having a dicarboxylic acid group represented by general formula (6). The lactone compounds represented by general formulae (7) to (10) are charged in 1.6- to 100-fold molar excess, more preferably 1.8- to 10-fold molar excess, even more preferably 2.0- to 6-fold molar excess, relative to the (meth)acrylate derivative having a dicarboxylic acid group represented by general formula (6). As a result, the (meth)acrylate compounds represented by general formula (1) can be obtained in high yield and without wasting the starting materials.

More specifically, to obtain the above (meth)acrylate compounds represented by general formula (1), the (meth)acrylate derivative having a dicarboxylic acid group represented by general formula (6) is generally reacted with the lactone compounds represented by general formulae (7) to (8) in the presence of a base catalyst. Examples of an organic base compound available for use as a catalyst include primary amines such as methylamine, ethylamine, propylamine, butylamine, s-butylamine, t-butylamine, pentylamine, hexylamine, cyclobutylamine, cyclopentylamine, cyclohexylamine, methoxymethylamine, ethoxymethylamine, and methoxyethylamine; secondary amines such as dimethylamine, diethylamine, dipropylamine, dibutylamine, dipentylamine, and dihexylamine; tertiary amines such as trimethylamine, triethylamine, tripropylamine, diisopropylethylamine, tributylamine, tripentylamine, and trihexylamine; aliphatic amines having an aromatic ring(s), such as aniline, N-methylaniline, N,N-dimethylaniline, diphenylamine, phenyldimethylamine, diphenylmethylamine, triphenylamine, and benzylamine; cycloaliphatic amines such as pyrrolidine, 1-methylpyrrolidine, 2-methylpyrrolidine, 3-methylpyrrolidine, proline, N-methylproline, 1-methylpiperidine, 2-methylpiperidine, 3-methylpiperidine, morpholine, 2-methylmorpholine, 3-methylmorpholine, and 4-methylmorpholine; amidines such as 1,8-diazabicyclo[5.4.0]-7-undecene, and 1,5-diazabicyclo[4.3.0]-5-nonene; guanidines such as guanidine, 1,1,3,3-tetramethylguanidine, and 1,2,3-triphenylguanidine; pyrroles such as pyrrole, 1-methylpyrrole, 2-methylpyrrole, 3-methylpyrrole, and 2,5-dimethylpyrrole; pyridines such as pyridine, 2-methylpyridine, 3-methylpyridine, 4-methylpyridine, 2,6-dimethylpyridine, and N,N-dimethyl-5-aminopyridine; quaternary ammonium salts such as tetramethylammonium hydroxide, and tetraethylammonium hydroxide, etc. The above catalysts may be used either alone or as a mixture of two or more of them. The amount to be added is 0.0001 to 20 equivalents, preferably 0.001 to 10 equivalents, and more preferably 0.005 to 3 equivalents, relative to the lactone compounds represented by general formulae (7) to (8).

In the reaction between the (meth)acrylate derivative having a dicarboxylic acid group represented by general formula (6) and the lactone compounds represented by general formulae (7) to (8), a solvent available for use may be exemplified by dimethyl sulfoxide, diethyl ether, diisopropyl ether, methyl-t-butyl ether, tetrahydrofuran, dioxane, dimethylacetamide, dimethylformamide, acetonitrile, benzene, toluene, xylene, mesitylene, pseudocumene, chloroform, chlorobenzene, dichloroethane, dichloromethane, acetone, methyl ethyl ketone, and methyl isobutyl ketone, although preparation is also possible in the absence of any solvent.

The (meth)acrylate derivative having a dicarboxylic acid group represented by general formula (6), the lactone compounds represented by general formulae (7) to (8) and the organic base compound(s) may be added in any order.

The reaction temperature and reaction time actually used for the above reaction will vary depending on the substrate concentration and the type of catalyst(s) to be used, although the above reaction may generally be conducted at a reaction temperature of −20° C. to 150° C., preferably 0° C. to 100° C., for a reaction time of 1 hour to 24 hours, preferably 1 hour to 10 hours, and under normal, reduced or elevated pressure. Moreover, the reaction may be conducted in any known mode selected as appropriate from batch, semi-batch and continuous modes, etc.

Alternatively, to obtain the above (meth)acrylate compounds represented by general formula (1), reaction is generally caused with the lactone compounds represented by general formulae (9) to (10) in the presence of an acid catalyst. Examples of an acid available for use as a catalyst include sulfuric acid, hydrochloric acid, nitric acid, benzenesulfonic acid, toluenesulfonic acid, cresolsulfonic acid and so on, with sulfuric acid and toluenesulfonic acid being preferred. The above catalysts may be used either alone or as a mixture of two or more of them. The amount to be added is 0.0001 to 20 equivalents, preferably 0.001 to 10 equivalents, and more preferably 0.005 to 1 equivalent, relative to the lactone compounds represented by general formulae (9) to (10).

In the reaction between the (meth)acrylate derivative having a dicarboxylic acid group represented by general formula (6) and the lactone compounds represented by general formulae (9) to (10), a solvent available for use may be exemplified by hexane, heptane, octane, nonane, decane, benzene, toluene, xylene, pseudocumene, mesitylene and other hydrocarbon compounds. Among them, toluene is preferred in terms of safety and easy handling.

The (meth)acrylate derivative having a dicarboxylic acid group represented by general formula (6), the lactone compounds represented by general formulae (9) to (10) and the acid catalyst(s) may be added in any order.

The reaction temperature and reaction time actually used for the above reaction will vary depending on the substrate concentration and the type of catalyst(s) to be used, although the reaction temperature will be equal to the boiling point of the solvent used because reflux dehydration generally occurs in this reaction. The above reaction may be conducted at a reaction temperature of 60° C. to 150° C., preferably 100° C. to 125° C., for a reaction time of 1 hour to 24 hours, preferably 1 hour to 10 hours, and under normal, reduced or elevated pressure. Moreover, the reaction may be conducted in any known mode selected as appropriate from batch, semi-batch and continuous modes, etc.

A series of reactions may be conducted in sequence or may be conducted continuously in the same reaction vessel without collecting any intermediate reaction product.

In addition, a polymerization inhibitor may be added during a series of reactions. Any polymerization inhibitor may be used for this purpose as long as it is commonly used, and examples include nitroso compounds such as 2,2,6,6-tetramethyl-4-hydroxypiperidine-1-oxyl, N-nitrosophenylhydroxylamine ammonium salt, N-nitrosophenylhydroxylamine aluminum salt, N-nitroso-N-(1-naphthyl)hydroxylamine ammonium salt, N-nitrosodiphenylamine, N-nitroso-N-methylaniline, nitrosonaphthol, p-nitrosophenol, and N,N'-dimethyl-p-nitrosoaniline; sulfur-containing compounds such as phenothiazine, methylene blue, and 2-mercaptobenzoimidazole; amines such as N,N'-diphenyl-p-phenylenediamine, N-phenyl-N'-isopropyl-p-phenylenediamine, 4-hydroxydiphenylamine, and aminophenol; quinones such as hydroxyquinoline, hydroquinone, methylhydroquinone, p-benzoquinone, and hydroquinone monomethyl ether; phenols such as p-methoxyphenol, 2,4-dimethyl-6-t-butylphenol, catechol, 3-s-butylcatechol, and 2,2-methylenebis-(6-t-butyl-4-methylphenol); imides such as N-hydroxyphthalimide; oximes such as cyclohexane oxime and p-quinone dioxime; dialkyl thiodipropionates and so on. The amount to be added is 0.001 to 10 parts by weight, preferably 0.01 to 1 part by weight, relative to 100 parts by weight of the (meth)acrylic group-containing compound. Further, to enhance the inhibitory effect on polymerization, oxygen may be bubbled into the reaction mixture.

The (meth)acrylate compounds represented by general formula (1) obtained on the basis of the foregoing descriptions are desirably isolated and purified as desired high purity monomers by known purification techniques, e.g., filtration, concentration, distillation, extraction, crystallization, recrystallization, column chromatography, separation and purification with the use of activated carbon or the like, or any combination of these techniques. This is because resist monomers are generally required to have a lower content of metal impurities. More specifically, the reaction mixture may be washed with water to remove excess starting materials and additives such as organic base compounds, inorganic salts, catalysts and so on. In this case, the water used for washing may comprise an appropriate inorganic salt such as sodium chloride or sodium bicarbonate. Further, acid washing may be conducted to remove metal impurities. For acid washing, inorganic acids such as aqueous hydrochloric acid, aqueous sulfuric acid and aqueous phosphoric acid, or organic acids such as aqueous oxalic acid may be used. During washing, an organic solvent or the like may be added to the reaction mixture. The organic solvent to be added may be the same as used for the reaction, or alternatively, a different organic solvent may be used for this purpose. However, it is generally preferable to use a less polar solvent which ensures good separation from water.

(Meth)acrylic copolymers obtainable by copolymerization of the (meth)acrylate compounds of the present invention represented by general formula (1) may be used in functional resins for use in photoresists. During copolymerization of the (meth)acrylate compounds represented by general formula (1) to obtain (meth)acrylic copolymers, these compounds may be used either alone or as a mixture.

The (meth)acrylic copolymers of the present invention preferably comprise, in addition to the repeating unit of general formula (11) derived from the (meth)acrylate compound of general formula (1), at least one repeating unit selected from general formulae (12) to (14). The (meth)acrylic copolymers of the present invention may further comprise a repeating unit(s) selected from general formulae (15) to (16) and general formula (17) in addition to general formula (11) and general formulae (12) to (14).

[Formula 44]

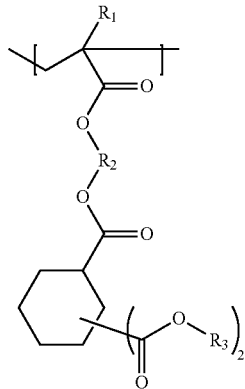

(11)

(wherein $R_1$ and $R_2$ are as defined in formula (1), and $R_3$ is represented by general formula (2) or (3) shown above)

[Formula 45]

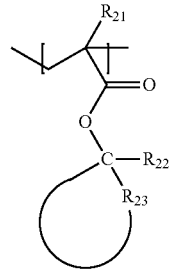

(12)

(wherein $R_{21}$ represents a hydrogen atom or a methyl group, $R_{22}$ represents an alkyl group containing 1 to 4 carbon atoms, and $R_{23}$ represents a cycloalkylene or cycloaliphatic alkylene group containing 5 to 20 carbon atoms)

[Formula 46]

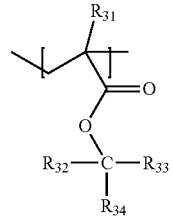

(13)

(wherein $R_{31}$ represents a hydrogen atom or a methyl group, $R_{32}$ to $R_{33}$, which may be the same or different, each represent an alkyl group containing 1 to 4 carbon atoms, and $R_{34}$ represents an alkyl group containing 1 to 4 carbon atoms or a cycloalkyl or cycloaliphatic alkyl group containing 5 to 20 carbon atoms)

[Formula 47]

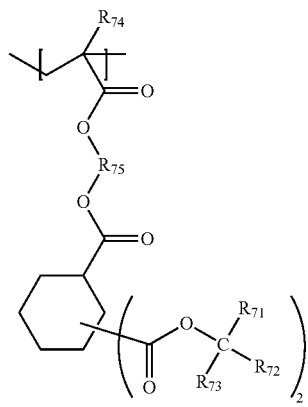

(14)

(wherein $R_{71}$ to $R_{73}$, which may be the same or different, each represent an alkyl group containing 1 to 4 carbon atoms or a cycloalkyl or cycloaliphatic alkyl group containing 5 to 20 carbon atoms, or $R_{72}$ and $R_{73}$ may be joined together to form a ring structure, $R_{74}$ represents a hydrogen atom or a methyl group, and $R_{75}$ represents a linear or branched alkylene group containing 2 to 4 carbon atoms)

[Formula 48]

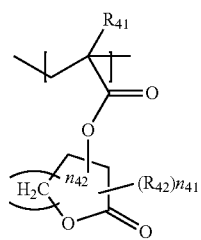

(15)

(wherein $R_{41}$ represents a hydrogen atom or a methyl group, $R_{42}$ represents a methyl group or an ethyl group, $n_{41}$ represents 0 to 2, and $n_{42}$ represents 1 to 3)

[Formula 49]

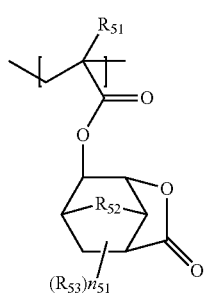

(16)

(wherein $R_{51}$ represents a hydrogen atom or a methyl group, $R_{52}$ represents methylene (—CH$_2$—) or oxa (—O—), if there are one or more $R_{53}$, each may be the same or different and independently represents a hydroxyl group, a halogen group, a nitrile group, a carboxylic acid group, an alkyl carboxylate group containing 1 to 4 carbon atoms or an alkoxide group containing 1 to 4 carbon atoms, and $n_{51}$ represents 0 to 2)

[Formula 50]

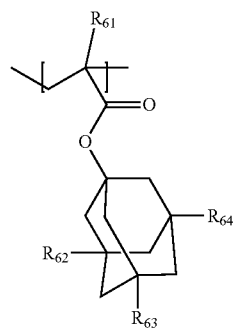

(17)

(wherein $R_{61}$ represents a hydrogen atom or a methyl group, and $R_{62}$ to $R_{64}$, which may be the same or different, each independently represent a hydrogen atom, a hydroxyl group, a methyl group or an ethyl group)

Examples of a starting material for the repeating unit represented by general formula (12) include 2-methyl-2-(meth)acryloyloxyadamantane, 2-ethyl-2-(meth)acryloyloxyadamantane, 2-isopropyl-2-(meth)acryloyloxyadamantane, 2-n-propyl-2-(meth)acryloyloxyadamantane, 2-n-butyl-2-(meth)acryloyloxyadamantane, 1-methyl-1-(meth)acryloyloxycyclopentane, 1-ethyl-1-(meth)acryloyloxycyclopentane, 1-methyl-1-(meth)acryloyloxycyclohexane, 1-ethyl-1-(meth)acryloyloxycyclohexane, 1-methyl-1-(meth)acryloyloxycycloheptane, 1-ethyl-1-(meth)acryloyloxycycloheptane, 1-methyl-1-(meth)acryloyloxycyclooctane, 1-ethyl-1-(meth)acryloyloxycyclooctane, 2-ethyl-2-(meth)acryloyloxydecahydro-1,4:5, 8-dimethanonaphthalene, 2-ethyl-2-(meth)acryloyloxynorbornane and so on.

Examples of a starting material for the repeating unit represented by general formula (13) include 2-cyclohexyl-2-(meth)acryloyloxypropane, 2-(4-methylcyclohexyo-2-(meth)acryloyloxypropane, 2-adamantyl-2-(meth)acryloyloxypropane, 2-(3-(1-hydroxy-1-methylethyl)adamantyl)-2-(meth)acryloyloxypropane and so on.

Examples of a starting material for the repeating unit represented by general formula (14) include the following formulae:

[Formula 51]

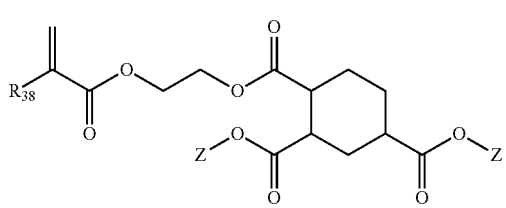

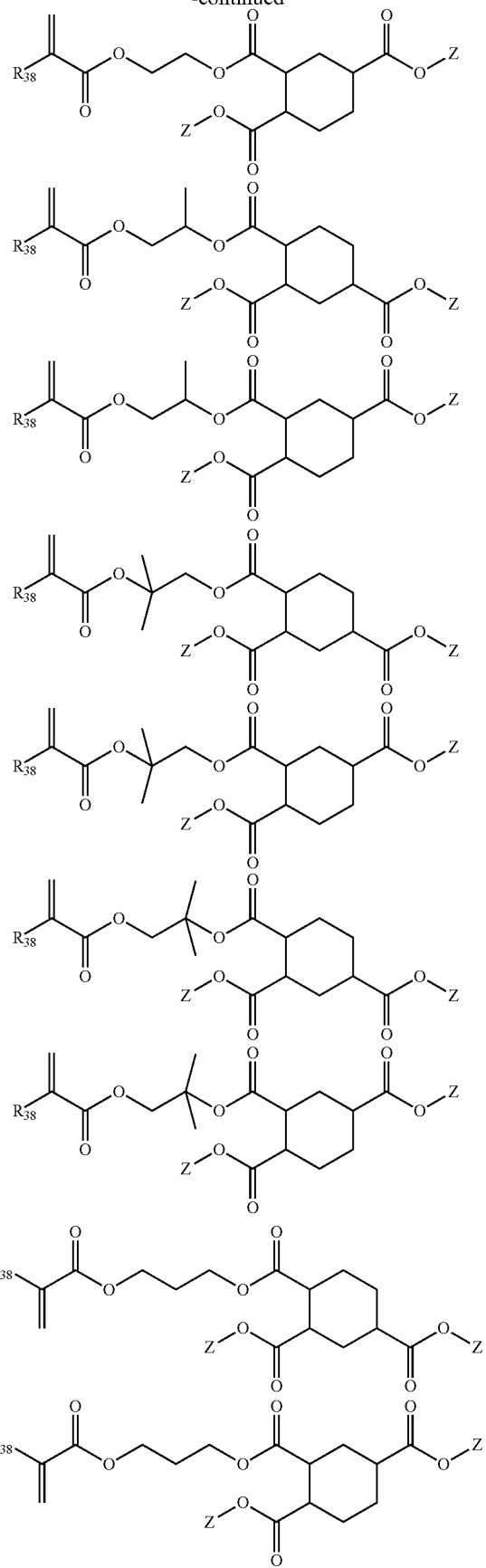
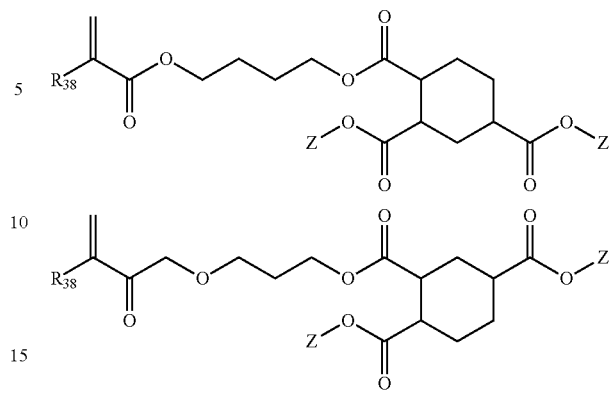
($R_{38}$ represents a hydrogen atom or a methyl group, and Z is represented by the following formulae).
[Formula 52]
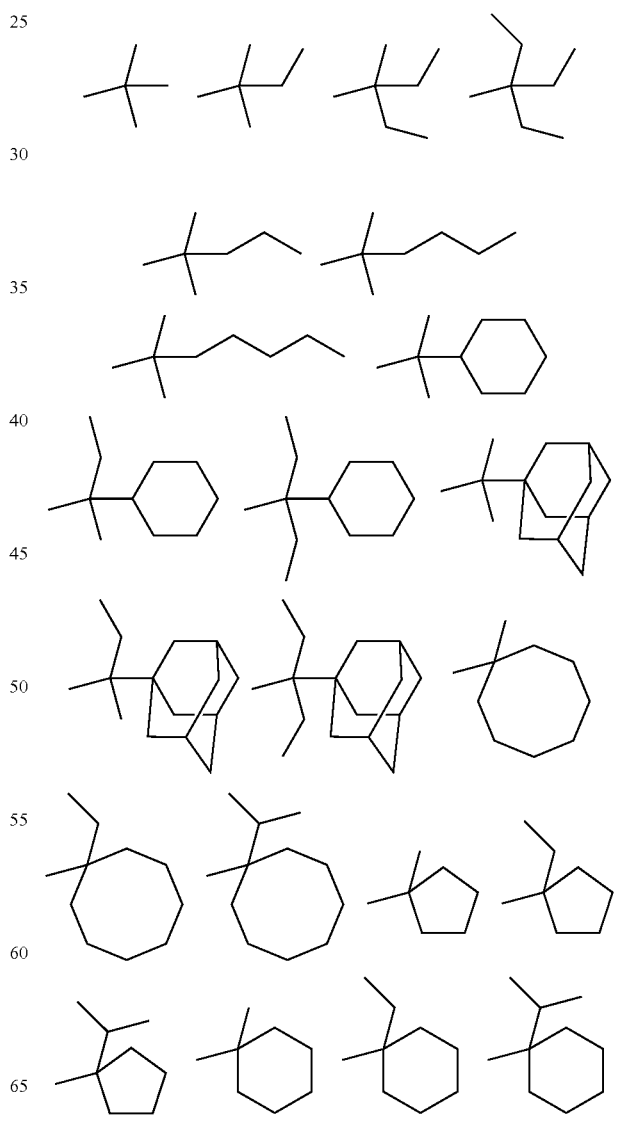

-continued

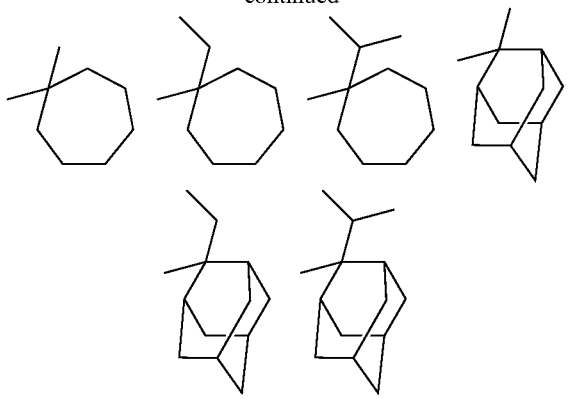

The repeating units represented by general formulae (12) to (14) have the function of being dissociable with an acid. In photoresists, as a result of comprising at least one repeating unit having the function of being dissociable with an acid, reaction will occur with an acid generated from a photoacid generator upon exposure to thereby produce a carboxylic acid group, which allows conversion into an alkali-soluble form.

Examples of a starting material for the repeating unit represented by general formula (15) include α-(meth)acryloyloxy-γ-butyrolactone, β-(meth)acryloyloxy-γ-butyrolactone, (meth)acryloyloxypantolactone and so on.

Examples of a starting material for the repeating unit represented by general formula (16) include 2-(meth)acryloyloxy-5-oxo-4-oxatricyclo[4.2.1.0$^{3,7}$]nonane, 7- or 8-(meth)acryloyloxy-3-oxo-4-oxatricyclo[5.2.1.0$^{26}$]decane, 9-(meth)acryloyloxy-3-oxo-2-oxa-6-oxa-tricyclo[4.2.1.0$^{4,8}$]nonane, 2-(meth)acryloyloxy-5-oxo-4-oxa-8-oxatricyclo[4.2.1.0$^{3,7}$]nonane, 2-(meth)acryloyloxy-9-methoxycarbonyl-5-oxo-4-oxatricyclo[4.2.1.0$^{3,7}$]nonane, 2-(meth)acryloyloxy-5-oxo-4-oxatricyclo[4.2.1.0$^{3,7}$]nonane-6-carbonitrile and so on.

The repeating units represented by general formulae (15) and (16) each have a lactone group, so that they are capable of improving the solubility in a solvent, the adhesion to a substrate and the affinity to an alkaline developer and can be used for photolithographic purposes. In this regard, the repeating units represented by general formulae (15) and (16) are almost equal in their performance. Since the repeating unit represented by general formula (11) already has a lactone group, the above performance can be adjusted by copolymerization with the repeating units represented by general formulae (15) and (16).

Examples of a starting material for the repeating unit represented by general formula (17) include 1-(meth)acryloyloxyadamantane, 3-hydroxy-1-(meth)acryloyloxy adamantane, 3,5-dihydroxy-1-(meth)acryloyloxyadamantane, 3,5-dimethyl-1-(meth)acryloyloxyadamantane, 5,7-dimethyl-3-hydroxy-1-(meth)acryloyloxyadamantane, 7-methyl-3,5-dihydroxy-1-(meth)acryloyloxyadamantane, 3-ethyl-1-(meth)acryloyloxyadamantane, 5-ethyl-3-hydroxy-1-(meth)acryloyloxyadamantane, 7-ethyl-3,5-dihydroxy-1-(meth)acryloyloxyadamantane and so on.

The repeating unit represented by general formula (17) is capable of further improving the solubility in a solvent, the adhesion to a substrate and the affinity to an alkaline developer. In particular, a repeating unit having a hydroxyl group(s) is generally capable of improving the resolution.

With regard to the copolymerization ratio in (meth)acrylic copolymers consisting of the repeating units represented by general formula (11) and general formulae (12) to (14), the repeating unit represented by general formula (11) preferably constitutes 20 to 80 mol %, more preferably 30 to 60 mol %, of all the repeating units (the remaining components are the repeating units represented by general formulae (12) to (14)). Moreover, in the case of also comprising the repeating unit represented by general formula (17), the ratio of general formula (11)/general formulae (12) to (14)/general formula (17) is preferably 20 to 50 mol %/20 to 50 mol %/10 to 20 mol % (provided that they constitute 100 mol % in total). In the case of comprising the repeating units represented by general formulae (15) and (16), they are used to substitute for a part of general formula (11) because they each have a lactone group, as in the case of general formula (11). The compositional ratio in this case is not limited in any way, but it is preferred that at least the repeating unit represented by general formula (11) constitutes 10 mol % or more of all the components because the sensitivity will be reduced when its content is less than 10 mol %. It should be noted that there is no limitation on the content of repeating units other than those of general formulae (11) to (17), but it is generally up to 30 mol % or less and more preferably held down to 20 mol % or less.

In general, polymerization may be accomplished as follows: monomers which form repeating units are dissolved in a solvent and reacted in the presence of a catalyst under heating or cooling conditions. Conditions used for the polymerization reaction may optionally be determined depending on the type of initiator, the mode of initiation (e.g., thermal or photo), temperature, pressure, concentration, the type of solvent, the type of additive(s), etc. In the case of the (meth)acrylic copolymers of the present invention, their polymerization may be accomplished in a known manner, e.g., by radical polymerization using a radical generator (e.g., azoisobutyronitrile, peroxide), ionic polymerization using a catalyst (e.g., alkyllithium, Grignard reagent), etc.

Examples of a solvent for use in the polymerization reaction of the (meth)acrylic copolymers of the present invention include ketones such as 2-butanone, 2-heptanone, methyl isobutyl ketone, and cyclohexanone; alkanes such as hexane, heptane, octane, cyclohexane, cyclooctane, decalin, and norbornane; alcohols such as methanol, ethanol, propanol, 2-propanol, n-butanol, sec-butanol, t-butanol, pentanol, hexanol, and propylene glycol monomethyl ether; ethers such as diethyl ether, tetrahydrofuran, and 1,4-dioxane; as well as carboxylic acid esters such as ethyl acetate, butyl acetate, methyl lactate, and propylene glycol monomethyl ether acetate. These solvents may be used either alone or as a mixture of two or more of them.

The (meth)acrylic copolymers of the present invention, e.g., (meth)acrylic copolymers comprising the above repeating units represented by general formulae (11) to (17) may be random copolymers, block copolymers or graft copolymers. Among them, random copolymers are preferred for the reason that it is possible to reduce defects upon exposure and/or line edge roughness.

The (meth)acrylic copolymers obtained in the present invention may be purified in a known manner. More specifically, for removal of metal impurities, ultrafiltration, microfiltration, acid washing, washing with water having an electric conductivity of 10 mS/m or less, and extraction may be conducted in any combination. In the case of acid washing, acids to be added include water-soluble acids, i.e., organic acids such as formic acid, acetic acid and propionic acid, as well as inorganic acids such as hydrochloric acid, sulfuric acid, nitric acid and phosphoric acid, with inorganic acids being preferred for use in terms of good separation from the reaction mixture. Likewise, for removal of oligomers, ultrafiltration, microfiltration, crystallization, recrystallization, extraction, washing with water having an electric conductivity of 10 mS/m or less and so on may be conducted in any combination.

The (meth)acrylic copolymers of the present invention have a weight average molecular weight calculated as polystyrene (hereinafter referred to as "Mw") of preferably 1,000 to 500,000, more preferably 3,000 to 100,000, as measured by gel permeation chromatography (GPC). Moreover, with regard to the ratio between Mw and number average molecular weight calculated as polystyrene (hereinafter referred to as "Mn") as measured by GPC, the (meth)acrylic copolymers generally have a Mw/Mn ratio of 1 to 10, preferably 1 to 5. Further, in the present invention, the (meth)acrylic copolymers may be used either alone or as a mixture of two or more of them.

In the photosensitive resin composition of the present invention, the above (meth)acrylic polymer(s) and a photoacid generator may be used by being dissolved in a solvent. Examples of a solvent commonly used for this purpose include linear ketones such as 2-pentanone and 2-hexanone; cyclic ketones such as cyclopentanone and cyclohexanone; propylene glycol monoalkyl acetates such as propylene glycol monomethyl ether acetate and propylene glycol monoethyl ether acetate; ethylene glycol monoalkyl ether acetates such as ethylene glycol monomethyl ether acetate and ethylene glycol monoethyl ether acetate; propylene glycol monoalkyl ethers such as propylene glycol monomethyl ether and propylene glycol monoethyl ether; ethylene glycol monoalkyl ethers such as ethylene glycol monomethyl ether and ethylene glycol monoethyl ether; diethylene glycol alkyl ethers such as diethylene glycol dimethyl ether and diethylene glycol diethyl ether; esters such as ethyl acetate and ethyl lactate; alcohols such as cyclohexanol and 1-octanol; as well as ethylene carbonate, γ-butyrolactone and so on. These solvents may be used either alone or as a mixture of two or more of them.

Depending on the wavelength of exposure light, a photoacid generator may be selected as appropriate from among those available for use as acid generators in chemically amplified resist compositions, in consideration of the range of resist coating thickness and the light absorption coefficient of the photoacid generator per se. Such photoacid generators may be used either alone or in combination of two or more of them. The amount of an acid generator(s) to be used is preferably 0.1 to 20 parts by weight, more preferably 0.5 to 15 parts by weight, relative to 100 parts by weight of the resin(s).

Examples of photoacid generators available for use in the far ultraviolet region include onium salt compounds, sulfonimide compounds, sulfone compounds, sulfonic acid ester compounds, quinone diazide compounds and diazomethane compounds, etc. Among them, onium salt compounds are preferred for KrF excimer lasers, EUV and electron beams, as exemplified by sulfonium salts, iodonium salts, phosphonium salts, diazonium salts, pyridinium salts, etc. Specific examples include triphenylsulfonium triflate, triphenylsulfonium nonafluorobutyrate, triphenylsulfonium hexafluoroantimonate, triphenylsulfonium naphthalenesulfonate, (hydroxyphenyl)benzylmethylsulfonium toluenesulfonate, diphenyliodonium triflate, diphenyliodonium pyrenesulfonate, diphenyliodonium dodecylbenzenesulfonate, diphenyliodonium hexafluoroantimonate and so on.

The photosensitive resin composition of the present invention may further comprise an acid diffusion inhibitor having the ability to prevent an acid(s) generated from the acid generator(s) upon exposure from diffusing into the resist coating and thereby inhibit unfavorable chemical reactions in the non-exposed regions. An acid diffusion inhibitor preferred for this purpose is a nitrogen-containing organic compound whose basicity is not affected by exposure and/or thermal treatment during resist pattern formation. Examples of such a nitrogen-containing organic compound include monoalkylamines such as n-hexylamine, n-heptylamine, and n-octylamine; dialkylamines such as di-n-butylamine; trialkylamines such as triethylamine; substituted trialcoholamines such as triethanolamine, tripropanolamine, tributanolamine, tripentanolamine, and trihexanolamine; trialkoxyalkylamines such as trimethoxyethylamine, trimethoxypropylamine, trimethoxybutylamine, and triethoxybutylamine; aromatic amines such as aniline, N,N-dimethylaniline, 2-methylaniline, 3-methylaniline, 4-methylaniline, 4-nitroaniline, and diphenylamine; amine compounds such as ethylenediamine; amide compounds such as formamide, N,N-dimethylformamide, N,N-dimethylacetamide, and N-methylpyrrolidone; urea compounds such as urea; imidazoles such as imidazole and benzimidazole; pyridines such as pyridine and 4-methylpyridine; as well as 1,4-diazabicyclo[2.2.2]octane and so on. The content of an acid diffusion inhibitor is generally 15 parts by weight or less, preferably 0.001 to 10 parts by weight, more preferably 0.005 to 5 parts by weight, relative to 100 parts by weight of the resin(s).

Furthermore, the photosensitive resin composition of the present invention may also optionally comprise various additives which have also been used in conventional chemically amplified resist compositions, as exemplified by surfactants, quenchers, sensitizers, antihalation agents, storage stabilizers, defoaming agents and so on.

To form a resist pattern from the photosensitive resin composition of the present invention, the composition solution prepared as described above may be applied onto a substrate (e.g., silicon wafer, metal, plastic, glass, ceramic) using an appropriate means such as a spin coater, a dip coater, a roller coater or the like to thereby form a resist coating, which is optionally pre-treated by heating at a temperature around 50° C. to 200° C., preferably 80° C. to 150° C., before exposure through a desired mask pattern. The thickness of the coating is, for example, about 0.01 to 5 μm, preferably about 0.02 to 1 μm, and more preferably about 0.02 to 0.1 μm. For exposure, light of various wavelengths, e.g., ultraviolet rays, X-rays and the like may be used. For example, far ultraviolet rays (e.g., an $F_2$ excimer laser (wavelength: 157 nm), an ArF excimer laser (wavelength: 193 nm), a KrF excimer laser (wavelength: 248 nm)), EUV (wavelength: 13 nm), X-rays, electron beams or the like may be selected as appropriate for use as a light source. Moreover, exposure conditions including the amount of exposure may be determined as appropriate, depending on the components and their ratio in the photosensitive resin composition, the type of each additive, etc.

In the present invention, for stable formation of high-resolution micropatterns, thermal treatment may preferably be conducted at a temperature of 50° C. to 200° C. for 30 seconds or longer after exposure. In this case, at a temperature of less than 50° C., the sensitivity will more widely vary depending on the type of substrate. The thermal treatment may be followed by development with an alkaline developer generally under conditions of 10° C. to 50° C. for 10 to 200 seconds, preferably 20° C. to 25° C. for 15 to 1200 seconds, to thereby form a desired resist pattern.

For use as the above alkaline developer, an alkaline compound such as an alkali metal hydroxide, aqueous ammonia, an alkylamine, an alkanolamine, a heterocyclic amine, a tetraalkylammonium hydroxide, choline, 1,8-diazabicyclo-[5.4.0]-7-undecene or 1,5-diazabicyclo-[4.3.0]-5-nonene may generally be dissolved at a concentration of 0.0001% to 10% by weight, preferably 0.01% to 5% by weight, more preferably 0.1% to 3% by weight, to prepare an aqueous alkaline solution. Moreover, the above developer containing an aqueous alkaline solution may further comprise a water-soluble organic solvent and/or a surfactant, as required.

The photosensitive resin composition of the present invention is excellent in adhesion to a substrate and is soluble in alkalis, and allows micropattern formation with high accuracy.

Among the (meth)acrylate compounds of the present invention, acid-dissociable ester compounds will be described in more detail below. The acid-dissociable ester compounds of the present invention are (meth)acrylate compounds represented by general formula (1) which have an acid-dissociable group represented by the above general formula (20) or (30) as $R_3$.

More specifically, the (meth)acrylate acid-dissociable ester compounds of the present invention may be exemplified as follows, but not limited thereto.

[Formula 53]

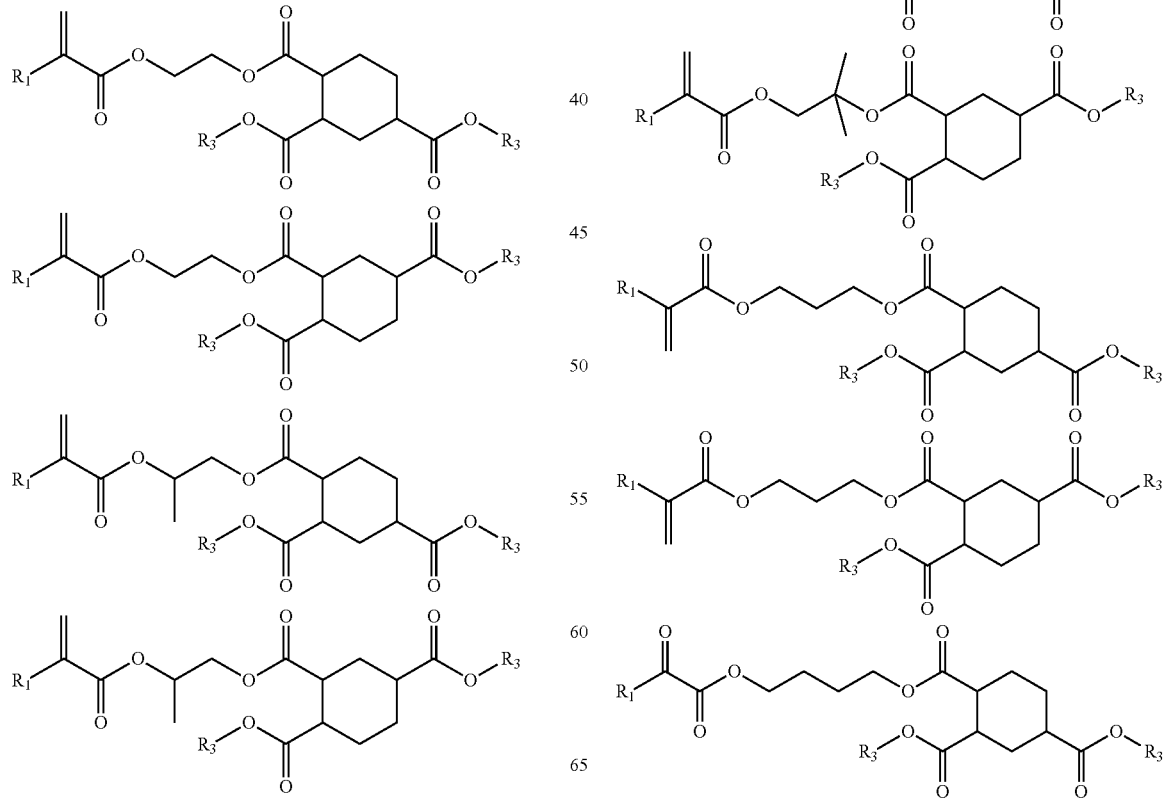

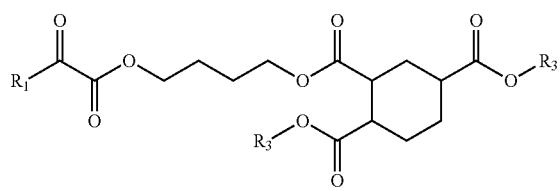

(wherein R₁ is a hydrogen atom or a methyl group, and R₃ may be exemplified as follows, but not limited thereto, provided that each R₃ may be the same or different)

[Formula 54]

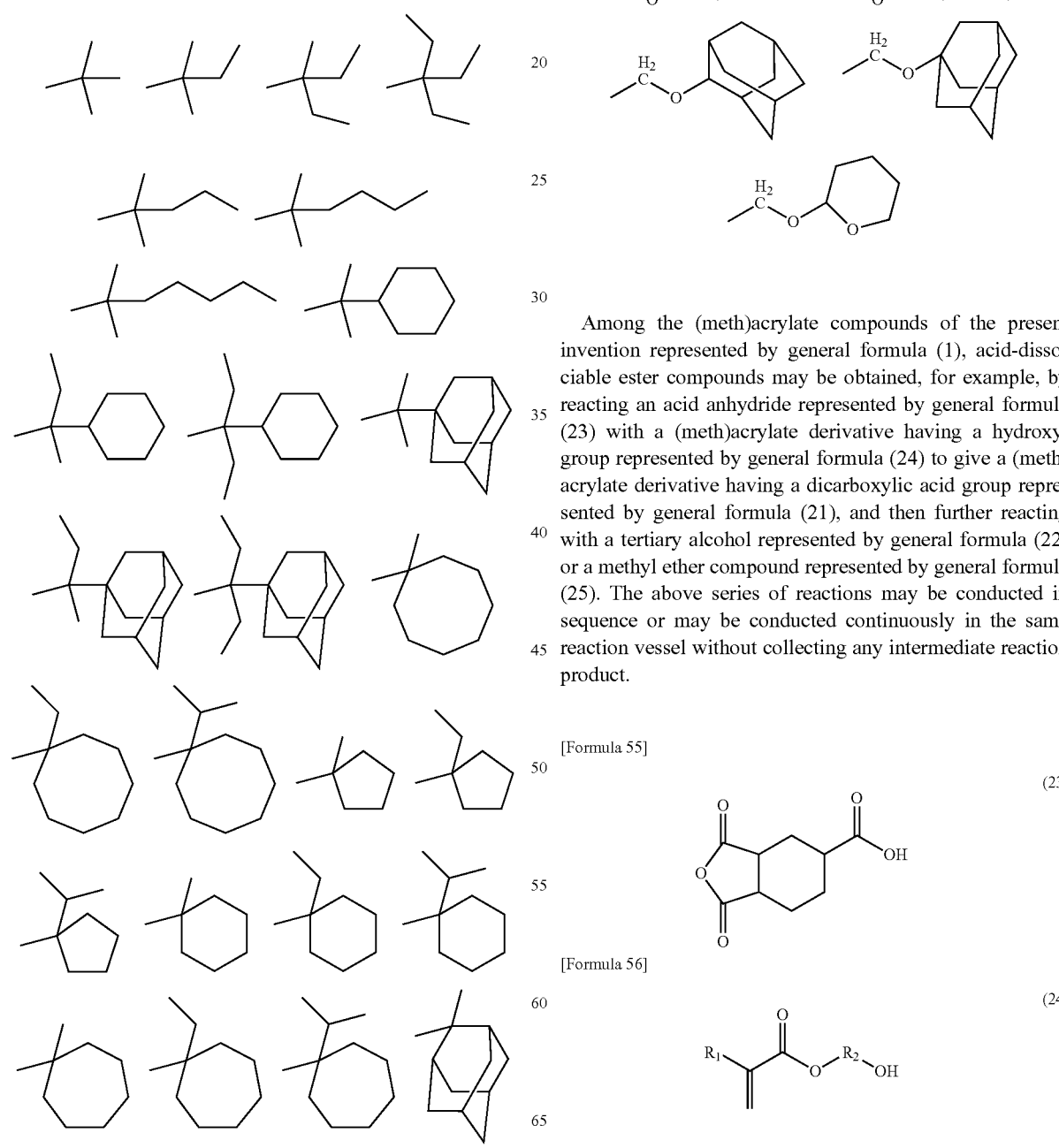

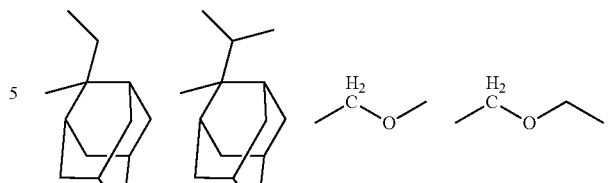

Among the (meth)acrylate compounds of the present invention represented by general formula (1), acid-dissociable ester compounds may be obtained, for example, by reacting an acid anhydride represented by general formula (23) with a (meth)acrylate derivative having a hydroxyl group represented by general formula (24) to give a (meth)acrylate derivative having a dicarboxylic acid group represented by general formula (21), and then further reacting with a tertiary alcohol represented by general formula (22) or a methyl ether compound represented by general formula (25). The above series of reactions may be conducted in sequence or may be conducted continuously in the same reaction vessel without collecting any intermediate reaction product.

[Formula 55]

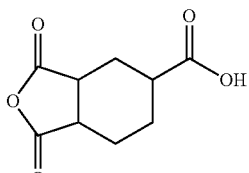

(23)

[Formula 56]

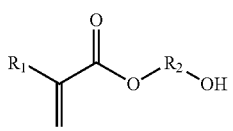

(24)

(wherein R₁ and R₂ are as defined in general formula (1))

[Formula 57]

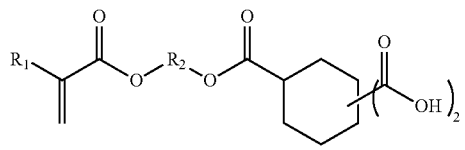

(21)

(wherein R₁ and R₂ are as defined in general formula (1))

[Formula 58]

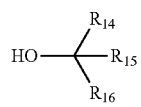

(22)

(wherein R₁₄ to R₁₆ are as defined in general formula (20))

[Formula 59]

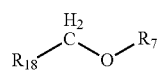

(25)

(wherein $R_7$ is as defined in general formula (30), and $R_{18}$ represents a halogen element)

Acid-dissociable ester compounds generated with the use of the compound of formula (22) or formula (25) are particularly suitable for use in photosensitive resin compositions. This is because in (co)polymers of the above acid-dissociable ester compounds, acid dissociation reaction will not proceed easily when compared to, for example, acid dissociation reaction in the hemiacetal structure which is generated upon addition of a vinyl ether to a carboxyl group. As a result, in photosensitive resin compositions comprising (co)polymers of the above acid-dissociable ester compounds together with a photoacid generator, protecting groups can be prevented reliably from unintended elimination reaction during pattern formation. For this reason, according to photosensitive resin compositions comprising (co)polymers of the above acid-dissociable ester compounds, protecting groups are selectively eliminated only in the exposed region to thereby ensure the formation of desired patterns.

The (meth)acrylate derivative having a hydroxyl group represented by general formula (24) to be used in the present invention may be exemplified by those listed above.

The (meth)acrylate derivative having a dicarboxylic acid group represented by general formula (21) to be used in the present invention may be exemplified by those listed above.

The tertiary alcohol represented by general formula (22) to be used in the present invention may be exemplified as follows.

[Formula 60]

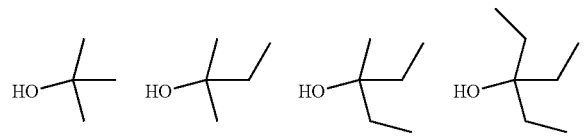

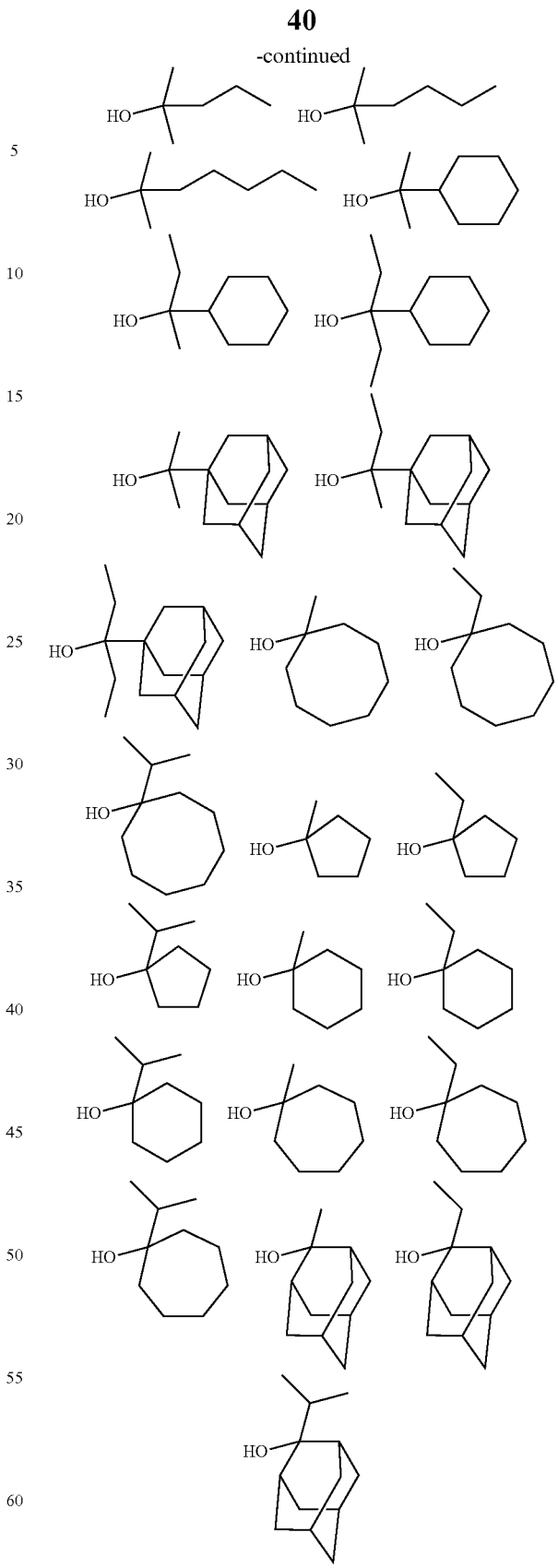

The methyl ether compound represented by general formula (25) to be used in the present invention may be exemplified as follows.

[Formula 61]

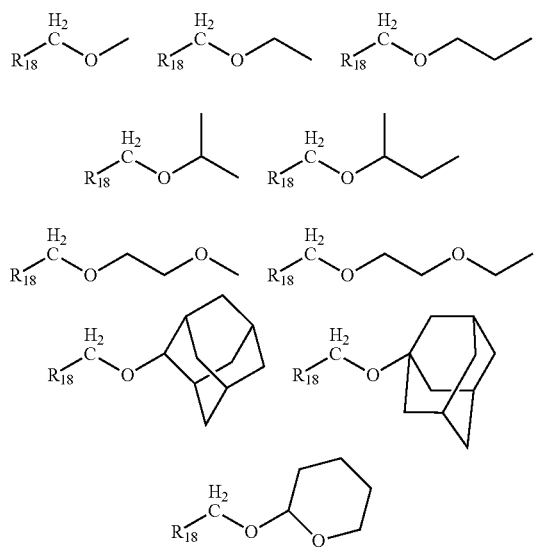

(wherein $R_{18}$ represents a halogen element)

How to prepare the (meth)acrylate acid-dissociable ester compounds of the present invention will be described in more detail. First, the reaction for obtaining the (meth) acrylate derivative having a dicarboxylic acid group represented by general formula (21) from the acid anhydride represented by general formula (23) and the (meth)acrylate derivative having a hydroxyl group represented by general formula (24) is a reaction in which 1 mole of acid anhydride is reacted with 1 mole of hydroxyl group to cause ring opening in the cyclic acid anhydride group to thereby generate 1 mole of carboxyl group. This ring-opening half ester reaction may be accomplished in a known manner, e.g., in the presence of an organic base compound added as a catalyst and in an organic solvent at a temperature ranging from 0° C. to 200° C., preferably from 0° C. to 100° C., more preferably from 0° C. to 50° C.

The (meth)acrylate derivative having a hydroxyl group represented by general formula (24) may be added in an amount of 0.5 to 5.0 equivalents, preferably 0.6 to 3.0 equivalents, more preferably 0.8 to 1.5 equivalents, relative to the acid anhydride represented by general formula (23). The amount within this range is also preferred in economical aspect because the reaction will proceed well and the desired product, i.e., the (meth)acrylate derivative having a dicarboxylic acid group represented by general formula (21) is obtained in high yield.

Examples of an organic base compound available for use as a catalyst include those listed above. The above catalysts may be used either alone or as a mixture of two or more of them. The amount to be added is 0.0001 to 20 equivalents, preferably 0.001 to 10 equivalents, and more preferably 0.005 to 3 equivalents, relative to the total number of moles of the carboxyl group substituted on the acid anhydride represented by general formula (21) and the carboxyl group generated from the acid anhydride upon reaction.

In the reaction intended in the present invention to obtain the (meth)acrylate derivative having a dicarboxylic acid group represented by general formula (21) from the acid anhydride represented by general formula (23) and the (meth)acrylate derivative having a hydroxyl group represented by general formula (24), a solvent available for use may be exemplified by those listed above, although preparation is also possible in the absence of any solvent.

The acid anhydride represented by general formula (23), the (meth)acrylate derivative having a hydroxyl group represented by general formula (24) and the organic base compound(s) may be added in any order. However, it is preferred that the (meth)acrylate derivative having a hydroxyl group represented by general formula (24) and the organic base compound(s) are dissolved in a solvent to prepare a solution and the cycloaliphatic acid anhydride represented by general formula (23) is then added thereto, because fewer by-products are generated in this order. The acid anhydride may be dissolved in a solvent and added dropwise or may be added without any solvent.

The reaction temperature and reaction time actually used for the above reaction will vary depending on the substrate concentration and the type of catalyst(s) to be used, although the above reaction may generally be conducted at a reaction temperature of −20° C. to 100° C., preferably 0° C. to 50° C., for a reaction time of 1 hour to 20 hours, preferably 1 hour to 10 hours, and under normal, reduced or elevated pressure. Moreover, the reaction may be conducted in any known mode selected as appropriate from batch, semi-batch and continuous modes, etc.

Among the (meth)acrylate compounds represented by general formula (1), acid-dissociable ester compounds may be obtained by reacting the (meth)acrylate derivative having a dicarboxylic acid group represented by general formula (21) with the tertiary alcohol represented by general formula (22) or the methyl ether compound represented by general formula (25).

Prior to the reaction with the tertiary alcohol represented by general formula (22), the (meth)acrylate derivative having a dicarboxylic acid group represented by general formula (21) may be treated to convert its two carboxyl groups into acid halides, whereby the reaction will proceed rapidly. Examples of a reagent required for conversion into acid halides include thionyl chloride, phosgene, oxalyl chloride and so on. Alternatively, the tertiary alcohol may be converted into an alcoholate form and then provided for reaction. Examples of a reagent required for conversion into an alcoholate form include alkali metals and alkali metal halides, etc. The reaction between the tertiary alcohol and the (meth)acrylate derivative having a dicarboxylic acid group represented by general formula (21) will proceed rapidly in the presence of an organic base compound in most cases.

On the other hand, the reaction between the methyl ether compound represented by general formula (25) and the (meth)acrylate derivative having a dicarboxylic acid group represented by general formula (21) is allowed to proceed rapidly in the presence of an organic base compound. In this case, without being isolated from the acid anhydride represented by general formula (23) and the (meth)acrylate derivative having a hydroxyl group represented by general formula (24), the (meth)acrylate derivative having a dicarboxylic acid group represented by general formula (21) may be reacted with the methyl ether compound represented by general formula (25) to thereby obtain the (meth)acrylate acid-dissociable ester compound represented by general formula (1).

The tertiary alcohol represented by general formula (22) or the methyl ether compound represented by general formula (25) is charged in 1.6- to 100-fold molar excess, more preferably 1.8- to 10-fold molar excess, even more preferably 2.0- to 6-fold molar excess, relative to the (meth)acrylate acid-dissociable ester compound represented by general formula (1). As a result, the acid-dissociable ester compounds represented by general formula (1) can be obtained in high yield and without wasting the starting materials.

To obtain acid-dissociable ester compounds among the above (meth)acrylate compounds represented by general formula (1), the reaction with the tertiary alcohol represented by general formula (22) or with the methyl ether compound represented by general formula (25) is conducted in the presence of a base catalyst. Examples of an organic base compound available for use as a catalyst include tertiary amines such as trimethylamine, triethylamine, tripropylamine, diisopropylethylamine, tributylamine, tripentylamine, and trihexylamine; aliphatic amines having an aromatic ring(s), such as N,N-dimethylaniline, phenyldimethylamine, diphenylmethylamine, and triphenylamine; cycloaliphatic amines such as 1-methylpyrrolidine, N-methylproline, 1-methylpiperidine, and 4-methylmorpholine; amidines such as 1,8-diazabicyclo[5.4.0]-7-undecene, and 1,5-diazabicyclo[4.3.0]-5-nonene; guanidines such as guanidine, 1,1,3,3-tetramethylguanidine, and 1,2,3-triphenylguanidine; aromatic amines such as 1-methylpyrrole, pyridine, 2-methylpyridine, 3-methylpyridine, 4-methylpyridine, 2,6-dimethylpyridine, and N,N-dimethyl-5-aminopyridine; quaternary ammonium salts such as tetramethylammonium hydroxide, and tetraethylammonium hydroxide, etc. The above catalysts may be used either alone or as a mixture of two or more of them. The amount to be added is 0.0001 to 20 equivalents, preferably 0.001 to 10 equivalents, and more preferably 0.005 to 3 equivalents, relative to the tertiary alcohol represented by general formula (24).

In the reaction between the (meth)acrylate derivative having a dicarboxylic acid group represented by general formula (21) and the tertiary alcohol represented by general formula (22) or the methyl ether compound represented by general formula (25), a solvent available for use may be exemplified by those listed above, although preparation is also possible in the absence of any solvent.

The (meth)acrylate derivative having a dicarboxylic acid group represented by general formula (21), the tertiary alcohol represented by general formula (22) or the methyl ether compound represented by general formula (25), and an organic base compound(s) may be added in any order.

The reaction temperature and reaction time actually used for the above reaction will vary depending on the substrate concentration and the type of catalyst(s) to be used, although the above reaction may generally be conducted at a reaction temperature of −20° C. to 100° C., for a reaction time of 1 hour to 10 hours, and under normal, reduced or elevated pressure. Moreover, the reaction may be conducted in any known mode selected as appropriate from batch, semi-batch and continuous modes, etc.

With regard to the preparation of acid-dissociable ester compounds, a series of reactions may be conducted in sequence or may be conducted continuously in the same reaction vessel without collecting any intermediate reaction product.

In addition, a polymerization inhibitor may be added during a series of reactions. The details of a polymerization inhibitor are as described above.

The (meth)acrylate acid-dissociable ester compounds represented by general formula (1) obtained on the basis of the foregoing descriptions are desirably isolated and purified as desired high purity monomers by known purification techniques, e.g., filtration, concentration, distillation, extraction, crystallization, recrystallization, column chromatography, separation and purification with the use of activated carbon or the like, or any combination of these techniques. This is because resist monomers are generally required to have a lower content of metal impurities. More details are as described above.

(Meth)acrylic copolymers obtainable by copolymerization of the (meth)acrylate acid-dissociable ester compounds represented by general formula (1) according to the present invention may be used in functional resins for use in photoresists. During copolymerization of the (meth)acrylate acid-dissociable ester compounds represented by general formula (1) to obtain (meth)acrylic copolymers, these compounds may be used either alone or as a mixture.

The (meth)acrylic copolymers of the present invention comprise general formula (26) derived from the (meth)acrylate compound of general formula (1) as a repeating unit and may further comprise at least one member selected from general formulae (27) to (28) as a repeating unit. Furthermore, the (meth)acrylic copolymers of the present invention may comprise a repeating unit(s) selected from general formulae (32) to (33) and general formula (34), in addition to the repeating units of general formula (26) and general formulae (27) to (28) or in place of the repeating units of general formulae (27) to (28).

[Formula 62]

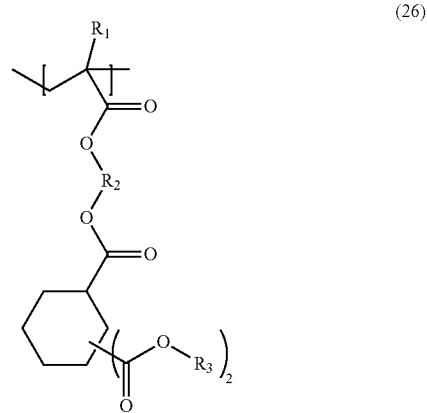

(26)

(wherein $R_1$ and $R_2$ are as defined in formula (1), and $R_3$ is represented by general formula (20) or (30) shown above)

[Formula 63]

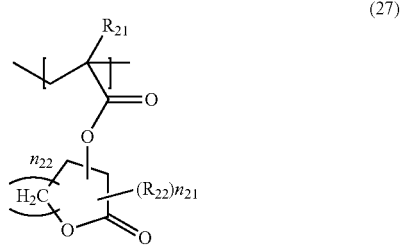

(27)

(wherein $R_{21}$ represents a hydrogen atom or a methyl group, $R_{22}$ represents a methyl group, an ethyl group, a hydroxyl group or a halogen group, $n_{21}$ represents 0 to 2, and $n_{22}$ represents 1 to 3)

[Formula 64]

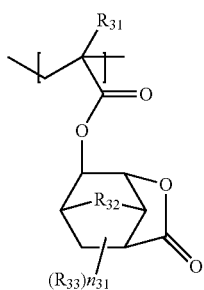

(28)

(wherein $R_{31}$ represents a hydrogen atom or a methyl group, $R_{32}$ represents methylene (—$CH_2$—) or oxa (—O—), each $R_{33}$ may be the same or different and independently represents a hydroxyl group, a halogen group, a nitrile group, a carboxylic acid group, an alkyl carboxylate group containing 1 to 4 carbon atoms or an alkoxide group containing 1 to 4 carbon atoms, and $n_{31}$ represents 0 to 2)

[Formula 65]

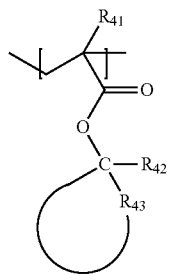

(32)

(wherein $R_{41}$ represents a hydrogen atom or a methyl group, $R_{42}$ represents an alkyl group containing 1 to 4 carbon atoms, and $R_{43}$ represents a cycloalkylene or cycloaliphatic alkylene group containing 5 to 20 carbon atoms)

[Formula 66]

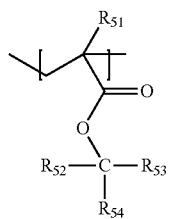

(33)

(wherein $R_{51}$ represents a hydrogen atom or a methyl group, $R_{52}$ to $R_{53}$, which may be the same or different, each independently represent an alkyl group containing 1 to 4 carbon atoms, and $R_{54}$ represents an alkyl group containing 1 to 4 carbon atoms or a cycloalkyl or cycloaliphatic alkyl group containing 5 to 20 carbon atoms)

[Formula 67]

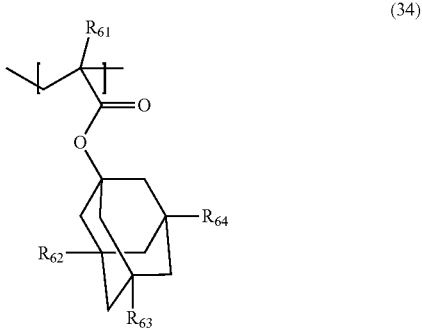

(34)

(wherein $R_{61}$ represents a hydrogen atom or a methyl group, and $R_{62}$ to $R_{64}$, which may be the same or different, each independently represent a hydrogen element, a hydroxyl group, a methyl group or an ethyl group)

Examples of a starting material for the repeating unit represented by general formula (27) include α-(meth)acryloyloxy-γ-butyrolactone, β-(meth)acryloyloxy-γ-butyrolactone, (meth)acryloyloxypantolactone and so on.

Examples of a starting material for the repeating unit represented by general formula (28) include 2-(meth)acryloyloxy-5-oxo-4-oxatricyclo[4.2.1.0$^{3,7}$]nonane, 7- or 8-(meth)acryloyloxy-3-oxo-4-oxatricyclo[5.2.1.0$^{2,6}$]decane, 9-(meth)acryloyloxy-3-oxo-2-oxa-6-oxa-tricyclo[4.2.1.0$^{4,8}$]nonane, 2-(meth)acryloyloxy-5-oxo-4-oxa-8-oxatricyclo[4.2.1.0$^{3,7}$]nonane, 2-(meth)acryloyloxy-9-methoxycarbonyl-5-oxo-4-oxatricyclo[4.2.1.0$^{3,7}$]nonane, 2-(meth)acryloyloxy-5-oxo-4-oxatricyclo[4.2.1.0$^{3,7}$]nonane-6-carbonitrile and so on.

The repeating units represented by general formulae (27) and (28) each have a lactone group, so that they are capable of improving the solubility in a solvent, the adhesion to a substrate and the affinity to an alkaline developer and can be used for photolithographic purposes. In particular, the repeating unit represented by general formula (26) is not sufficient in these functions and it is therefore necessary to comprise the repeating units represented by general formulae (27) and (28). It should be noted that these two units have almost the same functions, and at least one of them is sufficient to ensure these functions.

Examples of a starting material for the repeating unit represented by general formula (32) include 2-methyl-2-(meth)acryloyloxyadamantane, 2-ethyl-2-(meth)acryloyloxyadamantane, 2-isopropyl-2-(meth)acryloyloxyadamantane, 2-n-propyl-2-(meth)acryloyloxyadamantane, 2-n-butyl-2-(meth)acryloyloxyadamantane, 1-methyl-1-(meth)acryloyloxycyclopentane, 1-ethyl-1-(meth)acryloyloxycyclopentane, 1-methyl-1-(meth)acryloyloxycyclohexane, 1-ethyl-1-(meth)acryloyloxycyclohexane, 1-methyl-1-(meth)acryloyloxycycloheptane, 1-ethyl-1-(meth)acryloyloxycycloheptane, 1-methyl-1-(meth)acryloyloxycyclooctane, 1-ethyl-1-(meth)acryloyloxycyclooctane, 2-ethyl-2-(meth)acryloyloxydecahydro-1,4:5, 8-dimethanonaphthalene, 2-ethyl-2-(meth)acryloyloxynorbornane and so on.

Examples of a starting material for the repeating unit represented by general formula (33) include 2-cyclohexyl-2-(meth)acryloyloxypropane, 2-(4-methylcyclohexyo-2-(meth)acryloyloxypropane, 2-adamantyl-2-(meth)acryloyloxypropane, 2-(3-(1-hydroxy-1-methylethyl)adamantyl)-2-(meth)acryloyloxypropane and so on.

The repeating units represented by general formulae (32) and (33) have the function of being dissociable with an acid. Since the repeating unit represented by general formula (26) also has the function of being dissociable with an acid, the acid dissociation performance can be adjusted to be further increased by copolymerization with the repeating units represented by general formulae (32) and (33). The repeating units represented by general formulae (32) and (33) are almost equal in their acid dissociation performance. As a result of comprising at least one repeating unit having the function of being dissociable with an acid, reaction will occur with an acid generated from a photoacid generator upon exposure to thereby produce a carboxylic acid group, which allows conversion into an alkali-soluble form.

Examples of a starting material for the repeating unit represented by general formula (34) include 1-(meth)acryloyloxyadamantane, 3-hydroxy-1-(meth)acryloyloxyadamantane, 3,5-dihydroxy-1-(meth)acryloyloxyadamantane, 3,5-dimethyl-1-(meth)acryloyloxyadamantane, 5,7-dimethyl-3-hydroxy-1-(meth)acryloyloxyadamantane, 7-methyl-3,5-dihydroxy-1-(meth)acryloyloxyadamantane, 3-ethyl-1-(meth)acryloyloxyadamantane, 5-ethyl-3-hydroxy-1-(meth)acryloyloxyadamantane, 7-ethyl-3,5-dihydroxy-1-(meth)acryloyloxyadamantane and so on.

The repeating unit represented by general formula (34) is capable of further improving the solubility in a solvent, the adhesion to a substrate and the affinity to an alkaline developer. In particular, a repeating unit having a hydroxyl group(s) is generally capable of improving the resolution.

With regard to the copolymerization ratio in (meth)acrylic copolymers consisting of the repeating units represented by general formula (26) and general formulae (27) to (28), the repeating unit represented by general formula (26) preferably constitutes 20 to 80 mol %, more preferably 40 to 60 mol %, of all the repeating units (the remaining components are the repeating units represented by general formulae (27) to (28)). Moreover, in the case of also comprising the repeating unit represented by general formula (34), the ratio of general formula (26)/general formulae (27) to (28)/general formula (34) is preferably 20 to 50 mol %/20 to 50 mol %/10 to 30 mol % (provided that they constitute 100 mol % in total). In the case of comprising the repeating units represented by general formulae (32) to (33), they are used to substitute for a part of general formula (26) because they each have the function of being dissociable with an acid, as in the case of general formula (26). The compositional ratio in this case is not limited in any way, but it is preferred that at least the repeating unit represented by general formula (26) constitutes 10 mol % or more of all the components because the sensitivity will be reduced when its content is less than 10 mol %. Moreover, (meth)acrylic copolymers may comprise additional repeating units other than those of general formulae (26) to (28) and (32) to (34). The compositional ratio in this case is not limited in any way, but it is preferred that at least the repeating units of general formulae (26) to (28) and (32) to (34) constitute 50 mol % or more of all the components because the sensitivity will be reduced when the sum of general formulae (26) to (28) and (32) to (34) is less than 50 mol %.

In general, polymerization may be accomplished as follows: monomers which form repeating units are dissolved in a solvent and reacted in the presence of a catalyst under heating or cooling conditions. Conditions used for the polymerization reaction are as described above.

In the polymerization reaction of (meth)acrylic copolymers using acid-dissociable ester compounds among the (meth)acrylate compounds of the present invention, solvents available for use in this reaction are as described above.

The (meth)acrylic copolymers of the present invention, e.g., (meth)acrylic copolymers comprising the above repeating units represented by general formulae (26) to (28) and (32) to (34) may be random copolymers, block copolymers or graft copolymers. Among them, random copolymers are preferred for the reason that it is possible to reduce defects upon exposure and/or line edge roughness.

The (meth)acrylic copolymers obtained in the present invention using the acid-dissociable ester compounds may be purified in a known manner. More details are as described above.

In the (meth)acrylic copolymers obtained using the acid-dissociable ester compounds, their weight average molecular weight calculated as polystyrene (hereinafter referred to as "Mw") and ratio Mw/Mn, as measured by gel permeation chromatography (GPC), are as described above. Moreover, the (meth)acrylic copolymers obtained using the acid-dissociable ester compounds may also be used either alone or as a mixture of two or more of them.

In a photosensitive resin composition comprising the (meth)acrylate acid-dissociable ester compound(s) of the present invention, the above (meth)acrylic polymer(s) and a photoacid generator may be used by being dissolved in a solvent. More details are as described above.

Moreover, a photoacid generator and an acid diffusion inhibitor available for use together with the photosensitive resin composition comprising the (meth)acrylate acid-dissociable ester compound(s) are as described above.

Further, the photosensitive resin composition comprising the (meth)acrylate acid-dissociable ester compound(s) may also optionally comprise various additives which have also been used in conventional chemically amplified resist compositions, as exemplified by surfactants, quenchers, sensitizers, antihalation agents, storage stabilizers, defoaming agents and so on.

The step of resist pattern formation from the photosensitive resin composition comprising the acid-dissociable ester compound(s) is as described above.

Such a photosensitive resin composition comprising the acid-dissociable ester compound(s) is also excellent in adhesion to a substrate and is soluble in alkalis, and allows micropattern formation with high accuracy.

EXAMPLES

The present invention will be further described in more detail by way of the following examples, although the present invention is not limited in any way by the following examples. In the examples, it should be noted that novel (meth)acrylic compounds were determined for their purity and yield by high performance liquid chromatography (HPLC) and determined for their structure by $^1$H- and $^{13}$C-NMR. Measurement conditions for HPLC are as follows.

<HPLC Measurement Conditions>

Column: L-column 2 ODS (5 μm, 4.6 φ×250 mm, Chemicals Evaluation and Research Institute, Japan), developing solvent:acetonitrile/water=80/20 (v/v), flow rate: 1 ml/minute, column temperature: 40° C., detector: RI Preparation Example 1

Preparation of mixture (A-1) of 2-((2-(methacryloyloxy)ethoxy)cyclohexane-1,4-dicarboxylic acid and 1-((2-(methacryloyloxy)ethoxy)cyclohexane-2,4-dicarboxylic acid

[Formula 68]

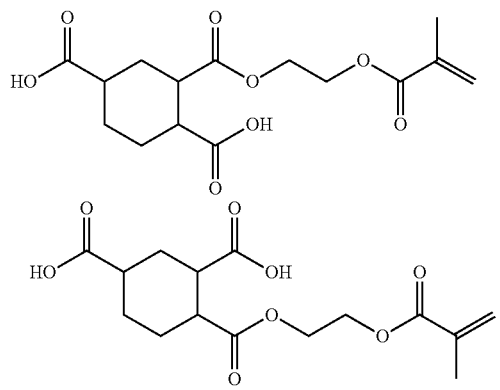

(A-1)

A 500 mL three-necked round-bottomed flask equipped with a dropping funnel, a stirrer and a thermometer was charged with dimethylaminopyridine (30.5 g, 250 mmol), and the reaction vessel was then purged with nitrogen. Subsequently, tetrahydrofuran (250 g), pyridine (41.5 g, 530 mmol) and 2-hydroxyethyl methacrylate (29.3 g, 225 mmol) were charged, and the reaction vessel was maintained in a water bath to ensure a solution temperature of 20° C. to 30° C. Cyclohexane-1,2,4-tricarboxylic acid-1,2-anhydride (49.5 g, 250 mmol) and tetrahydrofuran (375 g) were charged into the dropping funnel and added dropwise to the reaction vessel, followed by stirring at a solution temperature of 20° C. to 30° C. for 2 hours. After completion of the reaction, the precipitated white crystals were collected by suction filtration. The crystals were washed twice with tetrahydrofuran (100 g) and then dried under reduced pressure in a vacuum desiccator to obtain white crystals (98.0 g). To the resulting white crystals, ethyl acetate (500 g) and 5% aqueous sulfuric acid (500 g) were added for partition. The organic layer was further partitioned by addition of ion exchanged water (200 g), followed by collecting the organic layer. The solvent was distilled off to obtain white crystals of carboxylic acid mixture (A-1) (66.7 g, yield: 81.2%).

$^1$H-NMR spectrum (CDCl$_3$) for carboxylic acid mixture (A-1): δ 1.45 ppm (1H, m), 1.61 ppm (1H, m), 1.91 ppm (3H, s, methyl group in the methacryloyl group), 1.91 to 1.94 ppm (2H, m), 2.33 ppm (3H, m), 2.51 ppm (1H, m) 3.29 ppm (1H, m), 4.33 ppm (4H, m, —O—(CH$_2$)$_2$—O—), 5.7 ppm (1H, s, double bond in the methacryloyl group), 6.11 ppm (1H, s, double bond in the methacryloyl group).

$^{13}$C-NMR spectrum (CDCl$_3$) for carboxylic acid mixture (A-1): 18.2 ppm, 24.6 ppm, 26.0 ppm, 27.0 ppm, 40.8 ppm, 42.0 ppm, 42.2 ppm, 62.3 ppm, 62.5 ppm, 126.3 ppm, 135.8 ppm, 167.3 ppm, 172.7 ppm, 178.7 ppm, 180.6 ppm Example 1

Preparation of Lactone Compound 1 Isomer Mixture (L1)

[Formula 69]

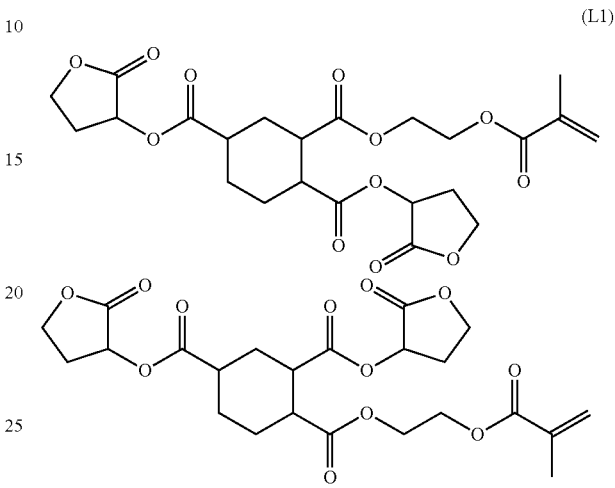

(L1)

A 100 mL three-necked round-bottomed flask equipped with a dropping funnel, a stirrer and a thermometer was charged with the white solid of (A-1) obtained in Preparation Example 1 (4.0 g, 12.2 mmol), toluene (40 g), phenothiazine (24 mg, 0.12 mmol), α-bromo-γ-butyrolactone (4.0 g, 24.4 mmol) and triethylamine (2.72 g, 26.8 mmol), followed by stirring at a solution temperature of 55° C. to 60° C. for 4 hours. After completion of the reaction, ion exchanged water (40 g) was added for partition. The organic layer was collected and the solvent was distilled off therefrom, followed by purification through silica gel column chromatography to obtain lactone compound 1 isomer mixture (L1) (5.0 g, yield: 81.7%).

Isomer 1 in L1

$^1$H-NMR spectrum (CDCl$_3$): δ 1.60 ppm (2H, m), 1.94 ppm (3H, s, methyl group in the methacryloyl group), 2.07 ppm (2H, m), 2.35 ppm (4H, m), 2.47 ppm (1H, m), 2.58 ppm (1H, m), 2.69 ppm (2H, m), 3.28 (1H, m), 4.2 ppm (2H, m) 4.34 ppm (4H, —O—(CH$_2$)$_2$—O—), 4.46 (2H, m) 5.43 ppm (2H, m), 5.59 ppm (1H, s, double bond in the methacryloyl group), 6.17 ppm (1H, s, double bond in the methacryloyl group).

$^{13}$C-NMR spectrum (CDCl$_3$): 18.3 ppm, 24.2 ppm, 26.0 ppm, 26.9 ppm, 28.7 ppm, 28.9 ppm, 40.2 ppm, 41.7 ppm, 42.4 ppm, 62.3 ppm, 62.6 ppm, 65.1 ppm, 65.2 ppm, 67.6 ppm, 67.8 ppm, 126.2 ppm, 135.9 ppm, 167.1 ppm, 171.7 ppm, 172.4 ppm, 172.5 ppm, 172.8 ppm, 173.3 ppm Isomer 2 in L1

$^1$H-NMR spectrum (CDCl$_3$): δ 1.64 ppm (2H, m), 1.93 ppm (3H, s, methyl group in the methacryloyl group), 2.04 ppm (2H, m), 2.35 ppm (4H, m), 2.47 ppm (1H, m), 2.57 ppm (1H, m), 2.69 ppm (2H, m), 3.30 (1H, m), 4.2 ppm (2H, m) 4.34 ppm (4H, —O—(CH$_2$)$_2$—O—), 4.46 (2H, m) 5.41 ppm (2H, m), 5.59 ppm (1H, s, double bond in the methacryloyl group), 6.17 ppm (1H, s, double bond in the methacryloyl group).

$^{13}$C-NMR spectrum (CDCl$_3$): 18.3 ppm, 24.4 ppm, 25.9 ppm, 26.9 ppm, 28.7 ppm, 28.9 ppm, 40.4 ppm, 41.7 ppm, 42.3 ppm, 62.3 ppm, 62.6 ppm, 65.0 ppm, 65.1 ppm, 67.6 ppm, 67.7 ppm, 126.2 ppm, 135.9 ppm, 167.1 ppm, 171.8 ppm, 172.3 ppm, 172.6 ppm, 172.8 ppm, 173.2 ppm

Example 2

One-Pot Synthesis of Lactone Compound 1 Isomer Mixture (L1)

A 200 mL three-necked round-bottomed flask equipped with a dropping funnel, a stirrer and a thermometer was charged with dimethylaminopyridine (6.1 g, 50 mmol), and the reaction vessel was then purged with nitrogen. Subsequently, tetrahydrofuran (50 g), pyridine (8.3 g, 105 mmol) and 2-hydroxyethyl methacrylate (5.86 g, 45 mmol) were charged, and the reaction vessel was maintained in a water bath to ensure a solution temperature of 20° C. to 30° C. Cyclohexane-1,2,4-tricarboxylic acid-1,2-anhydride (9.9 g, 50 mmol) and tetrahydrofuran (75 g) were charged into the dropping funnel and added dropwise to the reaction vessel, followed by stirring at a solution temperature of 20° C. to 30° C. for 2 hours. After completion of the reaction, phenothiazine (120 mg, 0.6 mmol) and α-bromo-γ-butyrolactone (20.0 g, 121 mmol) were added, followed by stirring at a solution temperature of 55° C. to 60° C. for 6 hours. After completion of the reaction, the reaction mixture was transferred to a separatory funnel and partitioned by addition of toluene (200 g) and ion exchanged water (200 g). The organic layer was collected and the solvent was distilled off therefrom, followed by purification through silica gel column chromatography to obtain lactone compound 1 isomer mixture (L1) (21.0 g, yield: 84.6%).

Example 3

Preparation of Lactone Compound 2 Isomer Mixture (L2)

[Formula 70]

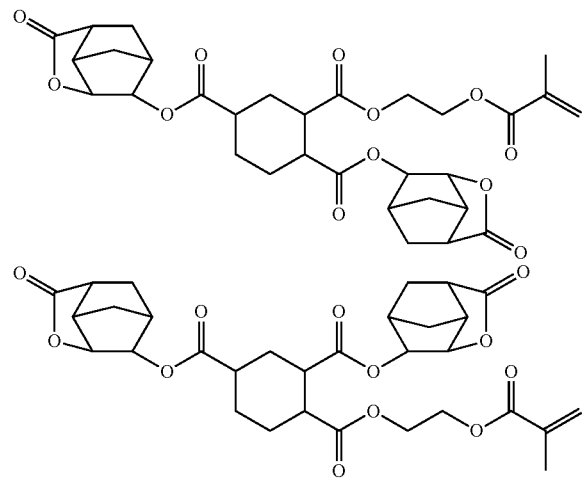

(L2)

A 100 mL three-necked round-bottomed flask equipped with a dropping funnel, a stirrer and a thermometer was charged with the white solid of (A-1) obtained in Preparation Example 1 (4.0 g, 12.2 mmol), toluene (40 g), p-methoxy-phenol (15 mg, 0.12 mmol) and 2-hydroxy-5-oxo-4-oxatricyclo[4.2.1.0$^{3,7}$]nonane (3.8 g, 24.4 mmol), followed by stirring at a solution temperature of 100° C. to 110° C. for 6 hours. After completion of the reaction, ion exchanged water (40 g) was added for partition. The organic layer was collected and the solvent was distilled off therefrom, followed by purification through silica gel column chromatography to obtain lactone compound 2 isomer mixture (L2) (2.3 g, yield: 32.0%).

Isomer 1 in L2

$^1$H-NMR spectrum (CDCl$_3$): δ 1.60 ppm (3H, m), 1.88 ppm (2H, m), 1.94 ppm (3H, s, methyl group in the methacryloyl group), 2.07 ppm (2H, m), 2.35 ppm (6H, m), 2.47 ppm (2H, m), 2.58 ppm (1H, m), 2.69 ppm (2H, m), 3.28 (1H, m), 4.2 ppm (2H, m) 4.34 ppm (4H, —O—(C$\underline{H}_2$)$_2$—O—), 4.46 (2H, m) 5.10 ppm (4H, m), 5.59 ppm (1H, s, double bond in the methacryloyl group), 6.17 ppm (1H, s, double bond in the methacryloyl group).

$^{13}$C-NMR spectrum (CDCl$_3$): 18.3 ppm, 24.2 ppm, 26.0 ppm, 26.9 ppm, 27.1 ppm, 27.2 ppm, 30.8 ppm, 30.9 ppm, 33.2 ppm, 33.3 ppm, 39.7 ppm, 39.9 ppm, 40.2 ppm, 41.7 ppm, 42.4 ppm, 45.9 ppm, 46.4 ppm, 62.3 ppm, 62.6 ppm, 72.6 ppm, 72.7 ppm, 75.4 ppm, 75.7 ppm, 126.2 ppm, 135.9 ppm, 167.1 ppm, 172.4 ppm, 172.8 ppm, 173.3 ppm, 178.2 ppm, 178.9 ppm Isomer 2 in L2

$^1$H-NMR spectrum (CDCl$_3$): δ 1.62 ppm (2H, m), 1.85 ppm (3H, m), 1.94 ppm (3H, s, methyl group in the methacryloyl group), 2.07 ppm (2H, m), 2.35 ppm (5H, m), 2.45 ppm (3H, m), 2.58 ppm (1H, m), 2.69 ppm (2H, m), 3.28 (1H, m), 4.2 ppm (2H, m) 4.34 ppm (4H, —O—(C$\underline{H}_2$)$_2$—O—), 4.46 (2H, m) 4.90 ppm (2H, m), 5.12 ppm (2H, m), 5.59 ppm (1H, s, double bond in the methacryloyl group), 6.17 ppm (1H, s, double bond in the methacryloyl group).

$^{13}$C-NMR spectrum (CDCl$_3$): 18.3 ppm, 24.2 ppm, 26.0 ppm, 26.8 ppm, 26.9 ppm, 27.2 ppm, 30.9 ppm, 31.0 ppm, 33.0 ppm, 33.3 ppm, 39.7 ppm, 40.0 ppm, 40.2 ppm, 41.7 ppm, 42.4 ppm, 45.9 ppm, 46.5 ppm, 62.3 ppm, 62.6 ppm, 72.6 ppm, 72.7 ppm, 75.4 ppm, 75.7 ppm, 126.2 ppm, 135.9 ppm, 171.1 ppm, 172.4 ppm, 172.8 ppm, 173.3 ppm, 178.2 ppm, 178.9 ppm

Example 4

Preparation of Acid-Dissociable Lactone Compound 1 Isomer Mixture (AL1)

[Formula 71]

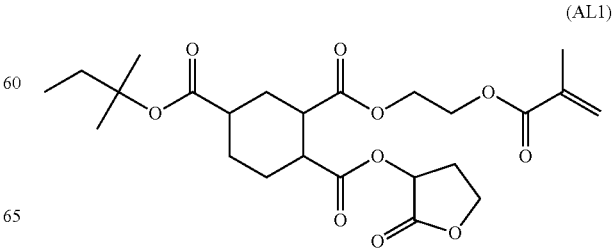

(AL1)

-continued

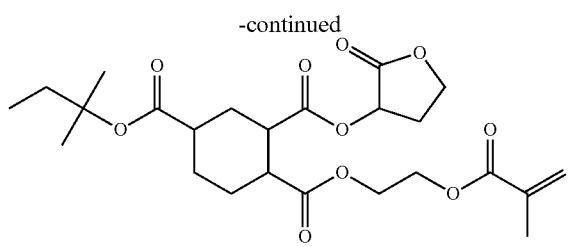

A 500 mL three-necked round-bottomed flask equipped with a dropping funnel, a stirrer and a thermometer was charged with the carboxylic acid mixture (A-1) synthesized in Preparation Example 1 (15.0 g, 46 mmol) and phenothiazine (92 mg, 0.46 mmol), and the reaction vessel was then purged with nitrogen. Subsequently, 1,2-dichloroethane (150 g) and dimethylformamide (0.34 g, 4.6 mmol) were charged, and the reaction vessel was maintained in a water bath to ensure a solution temperature of 20° C. to 30° C. Oxalyl chloride (12.8 g, 101 mmol) was charged into the dropping funnel and added dropwise to the reaction vessel. After stirring at a solution temperature of 20° C. to 30° C. for 3 hours, the solvent was distilled off from the reaction mixture to obtain a concentrate. A 500 mL three-necked round-bottomed flask equipped with a dropping funnel, a stirrer and a thermometer was purged with nitrogen and then charged with the resulting concentrate and 1,2-dichloroethane (30 g). Into the dropping funnel equipped to the 500 mL three-necked round-bottomed flask, 2-methyl-2-butanol (4.83 g, 55 mmol), pyridine (9.0 g, 114 mmol) and 1,2-dichloroethane (15 g) were introduced and then added dropwise to the reaction vessel, followed by stirring at a solution temperature of 20° C. to 35° C. After stirring for 1.5 hours, α-hydroxy-γ-butyrolactone (9.3 g, 91 mmol) was introduced into the dropping funnel and added dropwise to the reaction mixture, followed by stirring at a solution temperature of 20° C. to 35° C. for 20 hours. After completion of the reaction, the reaction mixture was partitioned by addition of ion exchanged water (150 g) and chloroform (155 g). The organic layer was partitioned by addition of 5% sodium bicarbonate (100 g). The organic layer was further partitioned by addition of ion exchanged water (100 g). The solvent was distilled off from the collected organic layer, followed by purification through silica gel column chromatography to obtain acid-dissociable lactone compound 1 isomer mixture (AL1) (14.5 g, yield: 65.7%).

Isomer 1 in AL1:
$^1$H-NMR spectrum (CDCl$_3$): δ 0.79 ppm (3H, t, —O—C(CH$_3$)$_2$CH$_2$CH$_3$), 1.35 ppm (6H, s, —O—C(CH$_3$)$_2$CH$_2$CH$_3$), 1.60 ppm (2H, m), 1.71 ppm (2H, q, —O—C(CH$_3$)$_2$CH$_2$CH$_3$), 1.94 ppm (3H, s, methyl group in the methacryloyl group), 2.07 ppm (2H, m), 2.35 ppm (2H, m), 2.47 ppm (1H, m), 2.58 ppm (1H, m), 2.69 ppm (2H, m), 3.33 (1H, m), 4.19 ppm (1H, m), 4.33 ppm (4H, —O—(CH$_2$)$_2$—O—), 4.45 (1H, m), 5.40 ppm (1H, m), 5.57 ppm (1H, s, double bond in the methacryloyl group), 6.10 ppm (1H, s, double bond in the methacryloyl group).

$^{13}$C-NMR spectrum (CDCl$_3$): 8.1 ppm, 18.3 ppm, 24.2 ppm, 26.0 ppm, 26.9 ppm, 28.7 ppm, 28.9 ppm, 33.3 ppm, 40.2 ppm, 41.7 ppm, 42.4 ppm, 62.3 ppm, 62.6 ppm, 65.1 ppm, 67.8 ppm, 83.0 ppm, 126.2 ppm, 135.9 ppm, 167.1 ppm, 171.7 ppm, 172.5 ppm, 172.9 ppm, 173.3 ppm.

Isomer 2 in AL1:
$^1$H-NMR spectrum (CDCl$_3$): δ 0.81 ppm (3H, t, —O—C(CH$_3$)$_2$CH$_2$CH$_3$), 1.34 ppm (6H, s, —O—C(CH$_3$)$_2$CH$_2$CH$_3$), 1.64 ppm (2H, m), 1.70 ppm (2H, q, —O—C(CH$_3$)$_2$CH$_2$CH$_3$), 1.93 ppm (3H, s, methyl group in the methacryloyl group), 2.04 ppm (2H, m), 2.35 ppm (2H, m), 2.47 ppm (1H, m), 2.57 ppm (1H, m), 2.69 ppm (2H, m), 3.26 (1H, m), 4.17 ppm (1H, m) 4.33 ppm (4H, —O—(CH$_2$)$_2$—O—), 4.45 (1H, m), 5.40 ppm (1H, m), 5.57 ppm (1H, s, double bond in the methacryloyl group), 6.10 ppm (1H, s, double bond in the methacryloyl group).

$^{13}$C-NMR spectrum (CDCl$_3$): 8.0 ppm, 18.3 ppm, 24.4 ppm, 25.9 ppm, 26.9 ppm, 28.7 ppm, 28.9 ppm, 33.4 ppm, 40.4 ppm, 41.7 ppm, 42.3 ppm, 62.3 ppm, 62.6 ppm, 65.1 ppm, 67.7 ppm, 82.9 ppm, 126.2 ppm, 135.9 ppm, 167.1 ppm, 171.8 ppm, 172.6 ppm, 172.8 ppm, 173.6 ppm Example 5

Resin Synthesis Example 1

The lactone compound 1 isomer mixture (L1) obtained in Example 1 (4.50 g), 2-ethyl-2-methacryloyloxyadamantane (hereinafter referred to as monomer A1; 2.19 g), 3-hydroxy-1-adamantyl methacrylate (hereinafter referred to as monomer B1; 0.99 g) and azobisisobutyronitrile (0.19 g) were dissolved in tetrahydrofuran (75 mL) and polymerized for 15 hours under a nitrogen atmosphere while maintaining the reaction temperature at 60° C. (the initial monomer ratio L1/A1/B1=40/40/20 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P1 (4.39 g).

Example 6

Resin Synthesis Example 2

The lactone compound 1 isomer mixture (L1) obtained in Example 1 (4.46 g), acid-dissociable ester compound 1 isomer mixture of the following formula (hereinafter referred to as monomer A2; 3.97 g) and azobisisobutyronitrile (0.15 g) were dissolved in tetrahydrofuran (85 mL) and polymerized for 15 hours under a nitrogen atmosphere while maintaining the reaction temperature at 60° C. (the initial monomer ratio L1/A2=50/50 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P2 (5.62 g). It should be noted that the preparation of monomer A2 will be described later (Example 17).

[Formula 72]

(A2)

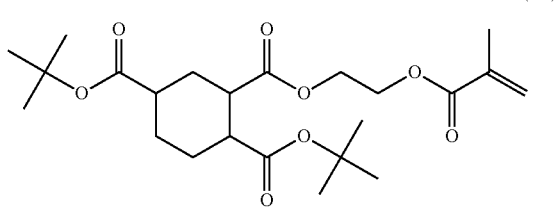

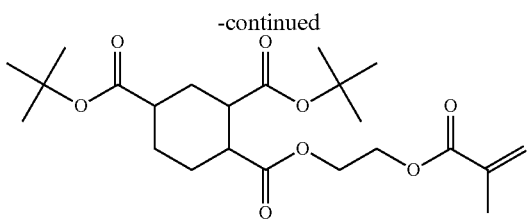

Example 7

Resin Synthesis Example 3

The lactone compound 1 isomer mixture (L1) obtained in Example 1 (4.50 g), 2-methacryloyloxy-2-(1-adamantyl)propane (hereinafter referred to as monomer A3; 2.31 g), 3-hydroxy-1-adamantyl methacrylate (hereinafter referred to as monomer B1; 0.99 g) and azobisisobutyronitrile (0.19 g) were dissolved in tetrahydrofuran (75 mL) and polymerized for 15 hours under a nitrogen atmosphere while maintaining the reaction temperature at 60° C. (the initial monomer ratio L1/A3/B1=40/40/20 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P3 (4.40 g).

Example 8

Resin Synthesis Example 4

The lactone compound 2 isomer mixture (L2) obtained in Example 3 (5.99 g), 2-ethyl-2-methacryloyloxyadamantane (hereinafter referred to as monomer A1; 2.19 g), 3-hydroxy-1-adamantyl methacrylate (hereinafter referred to as monomer B1; 0.99 g) and azobisisobutyronitrile (0.19 g) were dissolved in tetrahydrofuran (75 mL) and polymerized for 15 hours under a nitrogen atmosphere while maintaining the reaction temperature at 60° C. (the initial monomer ratio L2/A1/B1=40/40/20 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P4 (5.75 g).

Example 9

Resin Synthesis Example 5

The acid-dissociable lactone compound 1 isomer mixture (AL1) obtained in Example 4 (10.0 g) and azobisisobutyronitrile (0.15 g) were dissolved in tetrahydrofuran (85 mL) and polymerized for 15 hours under a nitrogen atmosphere while maintaining the reaction temperature at 60° C. (the initial monomer ratio AL1=100 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P5 (6.42 g).

Example 10

Resin Synthesis Example 6

The acid-dissociable lactone compound 1 isomer mixture (AL1) obtained in Example 4 (7.23 g), 3-hydroxy-1-adamantyl methacrylate (monomer B1; 0.99 g) and azobisisobutyronitrile (0.15 g) were dissolved in tetrahydrofuran (85 mL) and polymerized for 15 hours under a nitrogen atmosphere while maintaining the reaction temperature at 60° C. (AL1/B1=80/20 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P6 (6.42 g).

Examples 11, 12, 13, 14, 15 and 16

Evaluation of Resist Performance

The methacrylic copolymers P1 to P6, each in an amount of 100 parts by weight, and 10 parts by weight of triphenylsulfonium nonafluorobutanesulfonate (TPS-109, Midori Kagaku Co., Ltd., Japan) were dissolved in an ethyl lactate solvent to give a copolymer concentration of 6.3% by weight, thereby preparing photosensitive resin compositions $R_1$ to $R_6$. After an antireflection coating (ARC-29, Nissan Chemical Industries, Ltd., Japan) was applied onto a silicon wafer, each photoresist resin composition was applied onto the antireflection coating by spin coating to thereby form a photosensitive layer of 100 nm thickness. After pre-exposure bake on a hot plate at a temperature of 90° C. for 60 seconds, each photosensitive layer was irradiated in a 75 nm half-pitch line and space pattern (10 lines) using an electron beam lithography system (ELS-7700, Elionix Inc., Japan), followed by post-exposure bake (PEB) at a given temperature for 90 seconds. Then, each photosensitive layer was developed for 60 seconds with 0.3 M aqueous tetramethylammonium hydroxide and rinsed with pure water to obtain a line and space pattern.

Comparative Example 1

The same procedure as shown in Example 5 was repeated to obtain methacrylic copolymer P7 (14.1 g), except that monomer L1 was replaced with α-methacryloyloxy-γ-butyrolactone (hereinafter referred to as monomer L3) in an amount of 6.81 g (the initial monomer ratio L3/A1/B1=40/40/20 mol %).

Comparative Example 2

The same procedure as shown in Example 11 was repeated to prepare photosensitive resin composition R7, except that methacrylic copolymer P1 was replaced with methacrylic copolymer P7.

The resulting line and space patterns were observed by FE-SEM to determine their resolution and line edge roughness (LER). The results obtained are shown in Table 1. The photosensitive resin compositions R1 to R6 in Examples 11 to 16 were found to achieve a lower PEB temperature and ensure better LER and a higher resolution than R7 in Comparative Example 2.

Moreover, in terms of the difference in their lactone groups, R1 was found to achieve a lower PEB temperature and ensure a higher sensitivity than R7.

TABLE 1

| | Photosensitive Resin Composition | Copolymer | Monomers and Copolymers (molar ratio) | PEB temperature ° C. | Amount of exposure mC/cm$^2$ | Resolution nm | LER nm |
|---|---|---|---|---|---|---|---|
| Example 11 | R1 | P1 | L1/A1/B1 = 40/40/20 | 80 | 40 | 78 | 9.3 |
| Example 12 | R2 | P2 | L1/A2 = 50/50 | 70 | 35 | 74 | 9.0 |
| Example 13 | R3 | P3 | L1/A3/B1 = 40/40/20 | 90 | 40 | 76 | 8.0 |
| Example 14 | R4 | P4 | L2/A1/B1 = 40/40/20 | 90 | 40 | 75 | 7.8 |
| Example 15 | R5 | P5 | AL1 = 100 | 70 | 30 | 72 | 8.9 |
| Example 16 | R6 | P6 | AL1/B1 = 80/20 | 75 | 35 | 73 | 9.0 |
| Comparative Example 2 | R7 | P7 | L3/A1/B1 = 40/40/20 | 100 | 40 | 88 | 10.2 |

L1: Lactone compound 1 isomer mixture (L1) shown in Example 1
L2: Lactone compound 2 isomer mixture (L2) shown in Example 3
AL1: Acid-dissociable lactone 1 isomer mixture (AL1) shown in Example 4
L3: α-Methacryloyloxy-γ-butyrolactone
A1: 2-Ethyl-2-methacryloyloxyadamantane
A2: Acid-dissociable ester compound 1 isomer mixture (monomer A2)
A3: 2-Methacryloyloxy-2-(1-adamantyl)propane
B1: 3-Hydroxy-1-adamantyl methacrylate Example 17

Preparation of Acid-Dissociable Ester Compound 1 Isomer Mixture (A2)

[Formula 73]

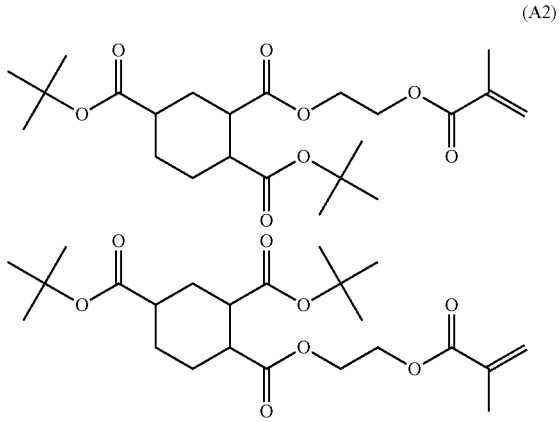

(A2)

A 200 mL three-necked round-bottomed flask equipped with a dropping funnel, a stirrer and a thermometer was charged with the carboxylic acid mixture (A-1) synthesized in Preparation Example 1 (15.0 g, 48 mmol), and the reaction vessel was then purged with nitrogen. Subsequently, 1,2-dichloroethane (150 g) and dimethylformamide (0.34 g, 4.8 mmol) were charged, and the reaction vessel was maintained in a water bath to ensure a solution temperature of 20° C. to 30° C. Oxalyl chloride (14.7 g, 116 mmol) was charged into the dropping funnel and added dropwise to the reaction vessel, followed by stirring at a solution temperature of 20° C. to 30° C. for 3 hours. A 500 mL three-necked round-bottomed flask equipped with a dropping funnel, a stirrer and a thermometer was purged with nitrogen and charged with 2-methyl-2-propanol (82.4 g, 1011 mmol) and triethylamine (12.7 g, 126 mmol). Into the dropping funnel equipped to the 500 mL three-necked round-bottomed flask, the above 1,2-dichloroethane solution was introduced and then added dropwise to the reaction vessel, followed by stirring at a solution temperature of 20° C. to 30° C. for 20 hours. After completion of the reaction, the reaction mixture was partitioned by addition of ion exchanged water (150 g) and ethyl acetate (150 g). The organic layer was collected and the solvent was distilled off therefrom, followed by purification through silica gel column chromatography to obtain acid-dissociable ester compound 1 isomer mixture (A2) (11.2 g, yield: 52.5%).

Isomer 1 in A2:
$^1$H-NMR spectrum (CDCl$_3$): δ 1.32 to 1.44 ppm (2H, m), 1.40 ppm (9H, s, t-butyl group), 1.41 ppm (9H, s, t-butyl group), 1.78 to 1.87 ppm (2H, m), 1.93 ppm (3H, s, methyl group in the methacryloyl group), 2.16 ppm (1H, m), 2.26 ppm (2H, m), 2.42 ppm (1H, m), 3.13 ppm (1H, m), 4.32 ppm (4H, —O—(CH$_2$)$_2$—O—), 5.57 ppm (1H, s, double bond in the methacryloyl group), 6.12 ppm (1H, s, double bond in the methacryloyl group).
$^{13}$C-NMR spectrum (CDCl$_3$): 18.3 ppm, 24.7 ppm, 26.6 ppm, 27.5 ppm, 27.9 ppm, 28.0 ppm, 41.7 ppm, 42.8 ppm, 43.6 ppm, 62.2 ppm, 62.4 ppm, 80.6 ppm, 81.1 ppm, 126.1 ppm, 135.1 ppm, 167.1 ppm, 171.8 ppm, 173.0 ppm, 174.2 ppm Isomer 2 in A2:
$^1$H-NMR spectrum (CDCl$_3$): δ 1.32 to 1.44 ppm (3H, m), 1.40 ppm (9H, s, t-butyl group), 1.42 ppm (9H, s, t-butyl group), 1.9 ppm (3H, s, methyl group in the methacryloyl group), 2.0 ppm (1H, m), 2.12 to 2.30 ppm (3H, m), 2.48 ppm (1H, m), 2.63 ppm (1H, m), 4.32 ppm (4H, —O—(CH$_2$)$_2$—O—), 5.57 ppm (1H, s, double bond in the methacryloyl group), 6.12 ppm (1H, s, double bond in the methacryloyl group).

$^{13}$C-NMR spectrum (CDCl$_3$): 18.3 ppm, 27.8 ppm, 27.9 ppm, 28.0 ppm, 28.1 ppm, 31.1 ppm, 43.2 ppm, 44.2 ppm, 45.0 ppm, 62.2 ppm, 62.4 ppm, 80.2 ppm, 80.4 ppm, 126.2 ppm, 135.8 ppm, 167.0 ppm, 173.7 ppm, 173.8 ppm, 174.1 ppm Isomer 3 in A2:

$^1$H-NMR spectrum (CDCl$_3$): δ 1.32 to 1.44 ppm (3H, m), 1.40 ppm (9H, s, t-butyl group), 1.42 ppm (9H, s, t-butyl group), 1.9 ppm (3H, s, methyl group in the methacryloyl group), 2.0 ppm (1H, m), 2.12 to 2.30 ppm (3H, m), 2.48 ppm (1H, m), 3.16 ppm (1H, m), 4.32 ppm (4H, —O—(CH$_2$)$_2$—O—), 5.57 ppm (1H, s, double bond in the methacryloyl group), 6.12 ppm (1H, s, double bond in the methacryloyl group).

$^{13}$C-NMR spectrum (CDCl$_3$): 18.3 ppm, 23.7 ppm, 25.0 ppm, 27.9 ppm, 28.0 ppm, 31.1 ppm, 39.5 ppm, 40.5 ppm, 43.4 ppm, 62.1 ppm, 62.2 ppm, 80.2 ppm, 80.5 ppm, 126.2 ppm, 135.8 ppm, 167.0 ppm, 173.1 ppm, 173.3 ppm, 174.5 ppm Example 18

Preparation of Acid-Dissociable Ester Compound 2 (A5)

[Formula 74]

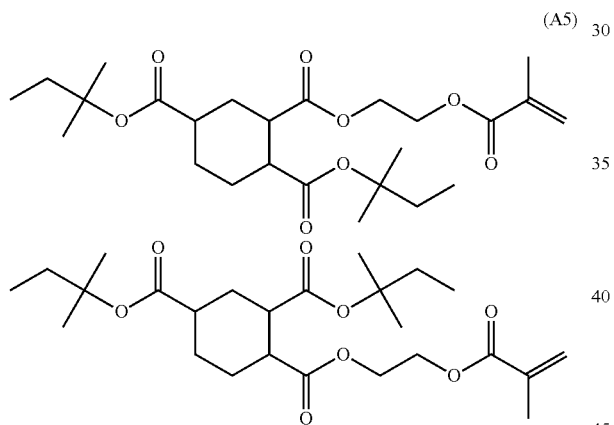

The same procedure as shown in Example 12 was repeated to obtain acid-dissociable ester compound 2 isomer mixture (A5) (5.4 g, yield: 25.4%), except that 2-methyl-2-propanol was replaced with 2-methyl-2-butanol (20.2 g, 229 mmol).

Isomer 1 in A5:

$^1$H-NMR spectrum (CDCl$_3$): δ 0.77 to 0.89 ppm (6H, t, —O—C(CH$_3$)$_2$CH$_2$CH$_3$), 1.32 to 1.44 ppm (2H, m), 1.33 ppm (6H, s, —O—C(CH$_3$)$_2$CH$_2$CH$_3$), 1.35 ppm (6H, s, —O—C(CH$_3$)$_2$CH$_2$CH$_3$), 1.71 ppm (4H, q, —O—C(CH$_3$)$_2$CH$_2$CH$_3$), 1.78 to 1.85 ppm (2H, m), 1.89 ppm (3H, s, methyl group in the methacryloyl group), 2.16 to 2.24 ppm (4H, m), 3.13 ppm (1H, m), 4.30 ppm (4H, —O—(CH$_2$)$_2$—O—), 5.53 ppm (1H, s, double bond in the methacryloyl group), 6.08 ppm (1H, s, double bond in the methacryloyl group).

$^{13}$C-NMR spectrum (CDCl$_3$): 8.1 ppm, 8.2 ppm, 18.2 ppm, 24.8 ppm, 25.4 ppm, 25.5 ppm, 26.5 ppm, 27.5 ppm, 33.2 ppm, 33.3 ppm, 41.7 ppm, 43.2 ppm, 43.7 ppm, 62.1 ppm, 62.4 ppm, 83.0 ppm, 83.7 ppm, 126.1 ppm, 135.9 ppm, 167.0 ppm, 171.8 ppm, 172.9 ppm, 174.0 ppm Isomer 2 in A5:

$^1$H-NMR spectrum (CDCl$_3$): δ 0.77 to 0.89 ppm (6H, t, —O—C(CH$_3$)$_2$CH$_2$CH$_3$), 1.32 to 1.44 ppm (3H, m), 1.32 ppm (6H, s, —O—C(CH$_3$)$_2$CH$_2$CH$_3$), 1.34 ppm (6H, s, —O—C(CH$_3$)$_2$CH$_2$CH$_3$), 1.70 ppm (4H, q, —O—C(CH$_3$)$_2$CH$_2$CH$_3$), 1.89 ppm (3H, s, methyl group in the methacryloyl group), 2.0 ppm (1H, m), 2.12 to 2.30 ppm (2H, m), 2.40 ppm (1H, m), 2.46 ppm (1H, m), 2.55 ppm (1H, m), 4.30 ppm (4H, —O—(CH$_2$)$_2$—O—), 5.53 ppm (1H, s, double bond in the methacryloyl group), 6.08 ppm (1H, s, double bond in the methacryloyl group).

$^{13}$C-NMR spectrum (CDCl$_3$): 8.0 ppm, 8.1 ppm, 18.2 ppm, 25.4 ppm, 25.5 ppm, 28.0 ppm, 28.2 ppm, 31.1 ppm, 33.3 ppm, 33.4 ppm, 42.7 ppm, 44.1 ppm, 45.0 ppm, 62.2 ppm, 62.3 ppm, 82.5 ppm, 82.9 ppm, 126.1 ppm, 135.9 ppm, 167.0 ppm, 173.5 ppm, 173.6 ppm, 174.1 ppm Isomer 3 in A5:

$^1$H-NMR spectrum (CDCl$_3$): δ 0.77 to 0.89 ppm (6H, t, —O—C(CH$_3$)$_2$CH$_2$CH$_3$), 1.32 to 1.44 ppm (3H, m), 1.32 ppm (6H, s, —O—C(CH$_3$)$_2$CH$_2$CH$_3$), 1.34 ppm (6H, s, —O—C(CH$_3$)$_2$CH$_2$CH$_3$), 1.70 ppm (4H, q, —O—C(CH$_3$)$_2$CH$_2$CH$_3$), 1.89 ppm (3H, s, methyl group in the methacryloyl group), 2.0 ppm (1H, m), 2.12 to 2.30 ppm (3H, m), 2.57 ppm (1H, m), 2.85 ppm (1H, m), 4.30 ppm (4H, —O—(CH$_2$)$_2$—O—), 5.53 ppm (1H, s, double bond in the methacryloyl group), 6.08 ppm (1H, s, double bond in the methacryloyl group).

$^{13}$C-NMR spectrum (CDCl$_3$): 8.0 ppm, 8.1 ppm, 18.2 ppm, 23.7 ppm, 25.4 ppm, 25.5 ppm, 26.5 ppm, 29.0 ppm, 33.2 ppm, 33.4 ppm, 39.3 ppm, 41.1 ppm, 44.5 ppm, 62.0 ppm, 62.1 ppm, 82.6 ppm, 83.0 ppm, 126.1 ppm, 135.8 ppm, 167.0 ppm, 173.2 ppm, 173.3 ppm, 174.4 ppm Example 19

Preparation of Acid-Dissociable Ester Compound 3 Isomer Mixture (A6)

[Formula 75]

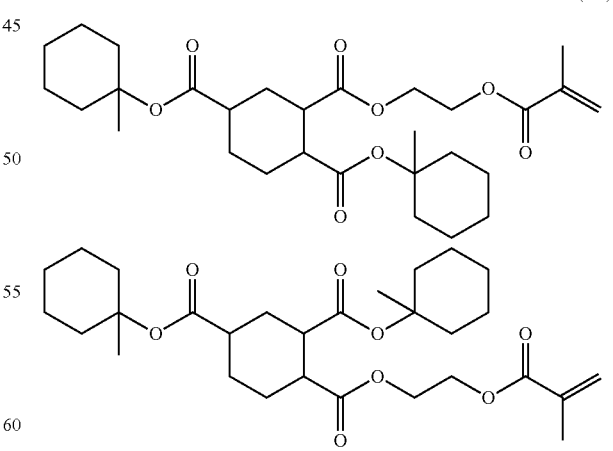

The same procedure as shown in Example 12 was repeated to obtain acid-dissociable ester compound 3 isomer mixture (A6) (2.2 g, yield: 9.0%), except that 2-methyl-2-propanol was replaced with 1-methyl-1-cyclohexanol (27.4 g, 230 mmol). Isomer mixture (A6):

¹H-NMR spectrum (CDCl₃): δ 1.20 to 1.54 ppm (20H, 1-methylcyclohexane ring), 1.41 ppm (3H, s, methyl group in the 1-methylcyclohexane ring), 1.43 ppm (3H, s, methyl group in the 1-methylcyclohexane ring), 1.93 ppm (3H, s, methyl group in the methacryloyl group), 1.85 to 1.98 ppm (2H, m), 2.09 ppm (2H, m), 2.25 ppm (1H, m), 2.31 ppm (2H, m), 2.43 ppm (1H, m), 3.19 ppm (1H, m), 4.31 ppm (4H, —O—(CH₂)₂—O—), 5.57 ppm (1H, s, double bond in the methacryloyl group), 6.10 ppm (1H, s, double bond in the methacryloyl group).

¹³C-NMR spectrum (CDCl₃): 18.3 ppm, 22.1 ppm, 22.2 ppm, 25.1 ppm, 25.4 ppm, 25.5 ppm, 26.8 ppm, 27.8 ppm, 36.5 ppm, 36.6 ppm, 36.7 ppm, 36.8 ppm, 42.4 ppm, 42.8 ppm, 43.8 ppm, 62.2 ppm, 62.5 ppm, 81.7 ppm, 83.0 ppm, 123.9 ppm, 135.9 ppm, 167.1 ppm, 171.9 ppm, 173.0 ppm, 173.9 ppm

Example 20

Preparation of Acid-Dissociable Ester Compound 4 Isomer Mixture (A7)

[Formula 76]

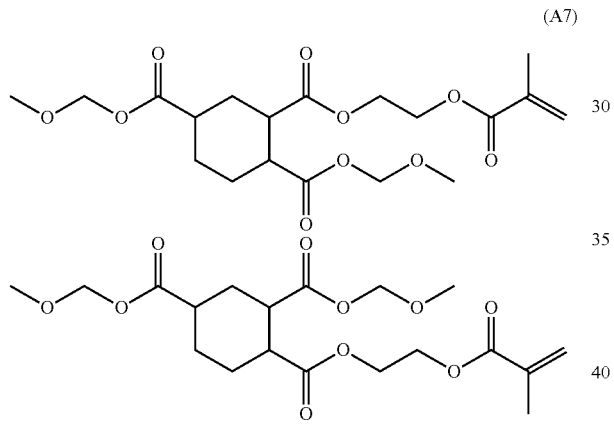

(A7)

A 200 mL three-necked round-bottomed flask equipped with a dropping funnel, a stirrer and a thermometer was charged with dimethylaminopyridine (4.7 g, 38 mmol), and the reaction vessel was then purged with nitrogen. Subsequently, tetrahydrofuran (38 g), pyridine (6.35 g, 81 mmol) and 2-hydroxyethyl methacrylate (4.5 g, 34 mmol) were charged, and the reaction vessel was maintained in a water bath to ensure a solution temperature of 20° C. to 30° C. Cyclohexane-1,2,4-tricarboxylic acid-1,2-anhydride (7.6 g, 38 mmol) and tetrahydrofuran (57 g) were charged into the dropping funnel and added dropwise to the reaction vessel, followed by stirring at a solution temperature of 20° C. to 30° C. for 2 hours. After completion of the reaction, the precipitated white crystals were collected by suction filtration. The crystals were washed twice with tetrahydrofuran (15 g) and then dried under reduced pressure in a vacuum desiccator to obtain white crystals (15 g, yield: 87.6%). A 200 mL three-necked round-bottomed flask equipped with a dropping funnel, a stirrer and a thermometer was charged with the resulting white solid, and the reaction vessel was then purged with nitrogen. Subsequently, the reaction vessel was charged with tetrahydrofuran (75 g) and triethylamine (9.1 g, 90 mmol), and then maintained in a water bath to ensure a solution temperature of 20° C. to 30° C. Chloromethyl ethyl ether (7.2 g, 90 mmol) was charged into the dropping funnel and added dropwise to the reaction vessel, followed by stirring at a solution temperature of 20° C. to 30° C. for 4 hours. After completion of the reaction, ion exchanged water (45 g) and ethyl acetate (80 g) were added for partition. The organic layer was collected and the solvent was distilled off therefrom, followed by purification through silica gel column chromatography to obtain acid-dissociable ester compound 4 isomer mixture (A7) (12.2 g, yield: 77.4%).

Isomer mixture (A7):

¹H-NMR spectrum (CDCl₃): δ 1.49 ppm (1H, m), 1.65 ppm (1H, m), 1.94 ppm (3H, s, methyl group in the methacryloyl group), 2.04 ppm (2H, m), 2.40 ppm (3H, m), 2.54 ppm (1H, m), 3.32 ppm (1H, m), 3.46 ppm (6H, s, —O—(CH₂)₂—OCH₃), 4.36 ppm (4H, —O—(CH₂)₂—O—), 5.19 to 5.27 ppm (4H, —O—(CH₂)₂—OCH₃), 5.59 ppm (1H, s, double bond in the methacryloyl group), 6.13 ppm (1H, s, double bond in the methacryloyl group).

¹³C-NMR spectrum (CDCl₃): 18.2 ppm, 24.5 ppm, 26.2 ppm, 27.0 ppm, 40.1 ppm, 42.3 ppm, 42.4 ppm, 62.2 ppm, 62.4 ppm, 90.5 ppm, 90.7 ppm, 126.0 ppm, 135.9 ppm, 1167.0 ppm, 172.3 ppm, 172.5 ppm, 174.0 ppm

Example 21

Resin Synthesis Example 8

The acid-dissociable ester compound 1 isomer mixture (A2) obtained in Example 17 (4.57 g), 3-hydroxy-1-adamantyl methacrylate (hereinafter referred to as monomer B1; 1.14 g), α-methacryloyloxy-γ-butyrolactone (hereinafter referred to as monomer L3; 1.72 g) and azobisisobutyronitrile (0.21 g) were dissolved in tetrahydrofuran (75 mL) and polymerized for 15 hours under a nitrogen atmosphere while maintaining the reaction temperature at 60° C. (the initial monomer ratio A2/B1/L3=40/20/40 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P8 (6.36 g).

Example 22

Resin Synthesis Example 9

The acid-dissociable ester compound 2 isomer mixture (A5) obtained in Example 18 (5.74 g), 3-hydroxy-1-adamantyl methacrylate (monomer B1; 1.32 g), α-methacryloyloxy-γ-butyrolactone (monomer L3; 1.98 g) and azobisisobutyronitrile (0.25 g) were dissolved in tetrahydrofuran (90 mL) and polymerized for 15 hours under a nitrogen atmosphere while maintaining the reaction temperature at 60° C. (the initial monomer ratio A5/B1/L3=40/20/40 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P9 (6.22 g).

Example 23

Resin Synthesis Example 10

The acid-dissociable ester compound 3 isomer mixture (A6) obtained in Example 19 (8.02 g), 3-hydroxy-1-adamantyl methacrylate (monomer B1; 1.82 g), α-methacryloyloxy-γ-butyrolactone (monomer L3; 2.73 g) and azobisisobutyronitrile (0.34 g) were dissolved in tetrahydrofuran (100 mL) and polymerized for 15 hours under a nitrogen atmosphere while maintaining the reaction temperature at 60° C. (the initial monomer ratio A6/B1/L3=40/20/40 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P10 (7.44 g).

Example 24

Resin Synthesis Example 11

The acid-dissociable ester compound 4 isomer mixture (A7) obtained in Example 20 (8.02 g), 3-hydroxy-1-adamantyl methacrylate (monomer B1; 1.82 g), α-methacryloyloxy-γ-butyrolactone (monomer L3; 2.73 g) and azobisisobutyronitrile (0.34 g) were dissolved in tetrahydrofuran (100 mL) and polymerized for 15 hours under a nitrogen atmosphere while maintaining the reaction temperature at 60° C. (the initial monomer ratio A7/B1/L3=40/20/40 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P11 (7.44 g).

Example 25

Resin Synthesis Example 12

The acid-dissociable ester compound 1 isomer mixture (A2) obtained in Example 17 (4.52 g), 3-hydroxy-1-adamantyl methacrylate (monomer B1; 1.12 g), 2-methacryloyloxy-5-oxo-4-oxatricyclo[4.2.1.0$^{3,7}$]nonane (hereinafter referred to as monomer L4; 2.20 g) and azobisisobutyronitrile (0.20 g) were dissolved in tetrahydrofuran (80 mL) and polymerized for 15 hours under a nitrogen atmosphere while maintaining the reaction temperature at 60° C. (the initial monomer ratio A2/B1/L4=40/20/40 mol %). After polymerization, the reaction mixture was added dropwise to 500 mL of n-hexane to thereby solidify and purify the resulting resin, and the generated white powder was filtered on a membrane filter and washed with n-hexane (1000 ml). The white powder was collected and dried overnight under reduced pressure at 40° C. to obtain methacrylic copolymer P12 (6.43 g).

Examples 26, 27, 28, 29 and 30

Evaluation of Resist Performance 100 parts by weight of the methacrylic copolymer P8, P9, P10, P11 or P12 and 10 parts by weight of triphenylsulfonium nonafluorobutanesulfonate (TPS-109, Midori Kagaku Co., Ltd., Japan) were dissolved in a propylene glycol-1-monomethyl ether-2-acetate (PGMEA) solvent to give a copolymer concentration of 6.3% by weight, thereby preparing photosensitive resin composition R8, R9, R10, R11 or R12. After an antireflection coating (ARC-29, Nissan Chemical Industries, Ltd., Japan) was applied onto a silicon wafer, each photoresist resin composition was applied onto the antireflection coating by spin coating to thereby form a photosensitive layer of 100 nm thickness. After pre-exposure bake on a hot plate at a temperature of 90° C. for 60 seconds, each photosensitive layer was irradiated in a 150 nm half-pitch line and space pattern (10 lines) using an electron beam lithography system (ELS-7700, Elionix Inc., Japan), followed by post-exposure bake (PEB) at a given temperature for 90 seconds. Then, each photosensitive layer was developed for 60 seconds with 0.3 M aqueous tetramethylammonium hydroxide and rinsed with pure water to obtain a line and space pattern.

Comparative Example 3

The same procedure as shown in Example 16 was repeated to obtain methacrylic copolymer P13 (6.85 g), except that monomer A2 was replaced with t-butyl methacrylate (hereinafter referred to as monomer A8) in an amount of 2.84 g (the initial monomer ratio A8/B1/L3=40/20/40 mol %).

Comparative Example 4

The same procedure as shown in Example 26 was repeated to prepare photosensitive resin composition R13, except that methacrylic copolymer P8 was replaced with methacrylic copolymer P13.

The resulting line and space patterns were observed by FE-SEM. The results obtained are shown in Table 2. The photosensitive resin compositions R8 to R12 in Examples 26 to 30 were found to achieve a lower PEB temperature and a lower amount of exposure and ensure a higher sensitivity than R13 in Comparative Example 4.

TABLE 2

| | Photosensitive Resin Composition | Copolymer | Monomers and Copolymers (molar ratio) | PEB temperature ° C. | Amount of exposure mC/cm$^2$ | Resolution nm |
|---|---|---|---|---|---|---|
| Example 26 | R8 | P8 | A2/B1/L3 = 40/20/40 | 100 | 40 | 150 |
| Example 27 | R9 | P9 | A5/B1/L3 = 40/20/40 | 100 | 35 | 146 |
| Example 28 | R10 | P10 | A6/B1/L3 = 40/20/40 | 100 | 35 | 147 |
| Example 29 | R11 | P11 | A7/B1/L3 = 40/20/40 | 110 | 40 | 146 |

TABLE 2-continued

| | Photosensitive Resin Composition | Copolymer | Monomers and Copolymers (molar ratio) | PEB temperature °C. | Amount of exposure mC/cm² | Resolution nm |
|---|---|---|---|---|---|---|
| Example 30 | R12 | P12 | A2/B1/L4 = 40/20/40 | 110 | 40 | 150 |
| Comparative Example 4 | R13 | P13 | AR/B1/L3 = 40/20/40 | 130 | 58 | 151 |

A2: Acid-dissociable ester compound 1 isomer mixture (A2) in t-Bu form shown in Example 17
A5: Acid-dissociable ester compound 2 isomer mixture (A5) in t-amyl form shown in Example 18
A6: Acid-dissociable ester compound 3 isomer mixture (A6) in methylcyclohexyl form shown in Example 19
A7: Acid-dissociable ester compound 4 isomer mixture (A7) in methoxymethyl form shown in Example 20
A8: t-Butyl methacrylate
B1: 3-Hydroxy-1-adamantyl methacrylate
L3: α-Methacryloyloxy-γ-butyrolactone
L4: 2-Methacryloyloxy-5-oxo-4-oxatricyclo[4.2.1.0³,⁷]nonane

The invention claimed is:

1. A (meth)acrylate compound represented by general formula (1):

[Formula 1]

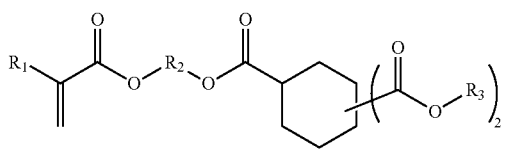

(1)

wherein R₁ represents a hydrogen atom or a methyl group, R₂ represents a linear or branched alkylene group containing 2 to 4 carbon atoms, and each R₃ may be the same or different and represents a group represented by the following formula (2), (3), (20) or (30)

[Formula 2]

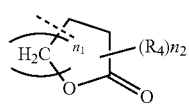

(2)

wherein each R₄ may be the same or different and independently represents a methyl group, an ethyl group, a hydroxyl group or a halogen group, n₁ represents 1 to 4, and n₂ represents 0 to 2

[Formula 3]

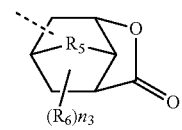

(3)

wherein R₅ may be either present or absent and if present, it represents methylene (—CH₂—) or oxa (—O—), if there are two or more R₆, each may be the same or different and independently represents a hydroxyl group, a halogen group, a nitrile group, a carboxylic acid group, an alkyl carboxylate group containing 1 to 4 carbon atoms or an alkoxide group containing 1 to 4 carbon atoms, and n₃ represents 0 to 2

[Formula 4]

(20)

wherein R₁₄, R₁₅ and R₁₆, which may be the same or different, each independently represent a cyclic, linear or branched alkyl group containing 1 to 13 carbon atoms, or R₁₅ and R₁₆ may be joined together to form a ring structure

[Formula 5]

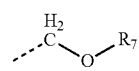

(30)

wherein R₇ represents a cyclic, linear or branched alkyl group containing 1 to 10 carbon atoms or an oxygen-containing cyclic, linear or branched alkyl group containing 1 to 10 carbon atoms.

2. A process for preparation of the (meth)acrylate compound of general formula (1) according to claim 1 wherein R₃ is represented by general formula (2) or (3), which comprises reacting an acid anhydride represented by general formula (4) with a (meth)acrylate derivative having a hydroxyl group represented by general formula (5) in the presence of an organic base to generate a (meth)acrylate derivative having a dicarboxylic acid group represented by general formula (6) and then allowing the (meth)acrylate derivative of general formula (6) to be directly provided, without being isolated, for reaction with a lactone compound represented by general formula (7) and/or (8):

[Formula 6]

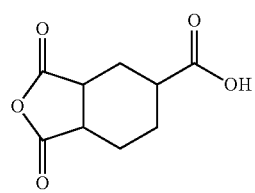

(4)

[Formula 7]

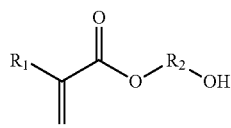

(5)

wherein $R_1$ and $R_2$ are as defined in general formula (1)

[Formula 8]

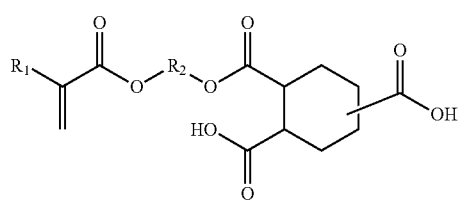

(6)

wherein $R_1$ and $R_2$ are as defined in general formula (1)

[Formula 9]

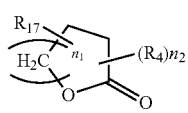

(7)

wherein $R_4$, $n_1$ and $n_2$ are as defined in general formula (2), and $R_{17}$ is a halogen group

[Formula 10]

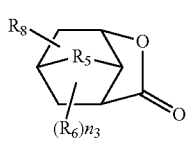

(8)

wherein $R_5$, $R_6$ and $n_3$ are as defined in general formula (3), and $R_8$ is a halogen group.

3. A process for preparation of the (meth)acrylate compound of general formula (1) according to claim 1 wherein $R_3$ is represented by general formula (2) or (3), which comprises reacting a (meth)acrylate derivative having a dicarboxylic acid group represented by general formula (6) with a lactone compound represented by general formula (9) and/or (10) in the presence of an acid catalyst:

[Formula 11]

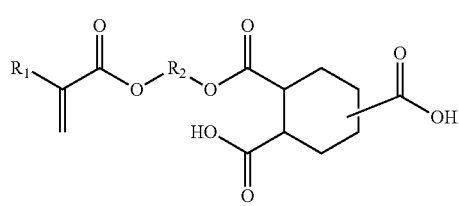

(6)

[Formula 12]

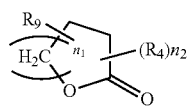

(9)

wherein $R_4$, $n_1$ and $n_2$ are as defined in general formula (2), and $R_9$ is a hydroxyl group

[Formula 13]

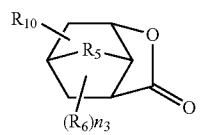

(10)

wherein $R_5$, $R_6$ and $n_3$ are as defined in general formula (3), and $R_{10}$ is a hydroxyl group.

4. A (meth)acrylic copolymer comprising general formula (11) as a repeating unit, which is obtainable by polymerization of the (meth)acrylate compound according to claim 1:

[Formula 14]

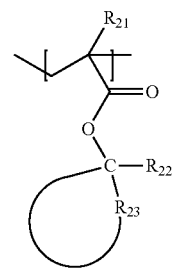

(11)

wherein $R_1$ and $R_2$ are as defined in general formula (1) shown above, and $R_3$ is represented by general formula (2) or (3) shown above.

5. The (meth)acrylic copolymer according to claim 4, which further comprises at least one member selected from general formulae (12) to (14) as a repeating unit, in addition to the repeating unit of general formula (11):

[Formula 15]

(12)

wherein $R_{21}$ represents a hydrogen atom or a methyl group, $R_{22}$ represents an alkyl group containing 1 to 4 carbon atoms, and $R_{23}$ represents a cycloalkylene or cycloaliphatic alkylene group containing 5 to 20 carbon atoms

[Formula 16]

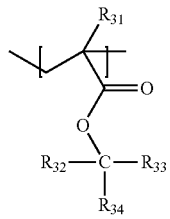

(13)

wherein $R_{31}$ represents a hydrogen atom or a methyl group, $R_{32}$ to $R_{33}$, which may be the same or different, each independently represent an alkyl group containing 1 to 4 carbon atoms, and $R_{34}$ represents an alkyl group containing 1 to 4 carbon atoms or a cycloalkyl or cycloaliphatic alkyl group containing 5 to 20 carbon atoms

[Formula 17]

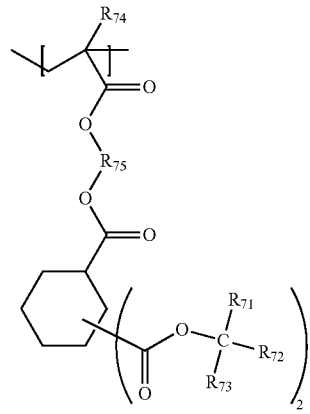

(14)

wherein $R_{71}$ to $R_{73}$, which may be the same or different, each represent an alkyl group containing 1 to 4 carbon atoms or a cycloalkyl or cycloaliphatic alkyl group containing 5 to 20 carbon atoms, or $R_{72}$ and $R_{73}$ may be joined together to form a ring structure, $R_{74}$ represents a hydrogen atom or a methyl group, and $R_{75}$ represents a linear or branched alkylene group containing 2 to 4 carbon atoms.

6. The (meth)acrylic copolymer according to claim 5, wherein the repeating unit of general formula (11) constitutes 20 to 80 mol % of all the repeating units.

7. A process for preparation of the (meth)acrylate compound of general formula (1) according to claim 1 wherein $R_3$ is represented by general formula (20), which comprises reacting a (meth)acrylate derivative having a dicarboxylic acid group represented by general formula (21) or an acid halide thereof with a tertiary alcohol represented by general formula (22) or an alcoholate thereof:

[Formula 18]

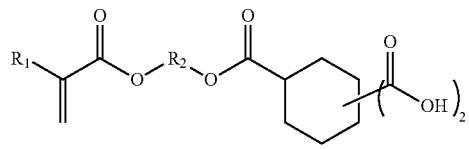

(21)

wherein $R_1$ represents a hydrogen atom or a methyl group, and $R_2$ represents a linear or branched alkyl group containing 2 to 4 carbon atoms

[Formula 19]

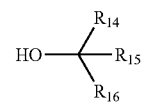

(22)

wherein $R_{14}$ to $R_{16}$ are as defined in general formula (20).

8. A process for preparation of the (meth)acrylate compound of general formula (1) according to claim 1 wherein $R_3$ is represented by general formula (30), which comprises reacting an acid anhydride represented by general formula (23) with a (meth)acrylate derivative having a hydroxyl group represented by general formula (24) in the presence of an organic base compound and then further reacting with a methyl ether compound represented by general formula (25):

[Formula 20]

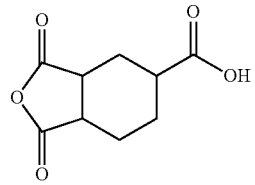

(23)

[Formula 21]

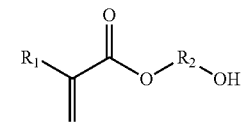

(24)

wherein $R_1$ and $R_2$ are as defined in general formula (1)

[Formula 22]

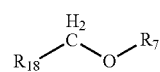

(25)

wherein $R_7$ is as defined in general formula (30), and $R_{18}$ represents a halogen element.

9. A (meth)acrylic copolymer comprising a repeating unit represented by general formula (26), which is obtainable by polymerization of the (meth)acrylate compound according to claim 1:

[Formula 23]

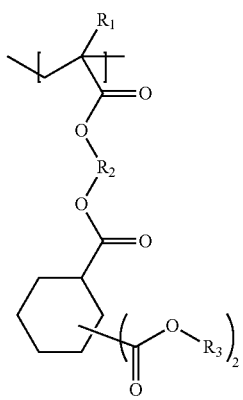

(26)

wherein $R_1$ and $R_2$ are as defined in general formula (1) shown above, and $R_3$ is represented by general formula (20) or (30) shown above.

10. The (meth)acrylic copolymer according to claim 9, which further comprises at least one member selected from general formulae (27) to (28) as a repeating unit, in addition to the repeating unit of general formula (26):

[Formula 24]

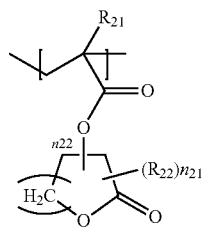

(27)

wherein $R_{21}$ represents a hydrogen atom or a methyl group, $R_{22}$ represents a methyl group, an ethyl group, a hydroxyl group or a halogen group, $n_{21}$ represents 0 to 2, and $n_{22}$ represents 1 to 3

[Formula 25]

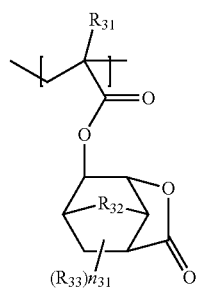

(28)

wherein $R_{31}$ represents a hydrogen atom or a methyl group, $R_{32}$ represents methylene ($-CH_2-$) or oxa ($-O-$), each $R_{33}$ may be the same or different and independently represents a hydroxyl group, a halogen group, a nitrile group, a carboxylic acid group, an alkyl carboxylate group containing 1 to 4 carbon atoms or an alkoxide group containing 1 to 4 carbon atoms, and $n_{31}$ represents 0 to 2.

11. The (meth)acrylic copolymer according to claim 10, wherein the repeating unit of general formula (26) constitutes 20 to 80 mol % of all the repeating units.

12. A process for preparation of the (meth)acrylate compound according to claim 1 wherein $R_3$ is represented by general formula (2) or (3) and is represented by general formula (20), which comprises reacting a (meth)acrylate derivative having a dicarboxylic acid group represented by general formula (21) or an acid halide thereof with a tertiary alcohol represented by general formula (22) or an alcoholate thereof and then further reacting with a lactone compound represented by general formula (9) and/or (10):

[Formula 26]

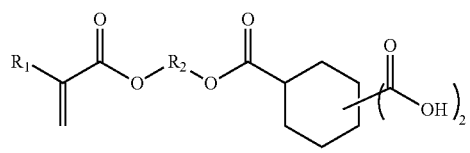

(21)

wherein $R_1$ represents a hydrogen atom or a methyl group, and $R_2$ represents a linear or branched alkyl group containing 2 to 4 carbon atoms

[Formula 27]

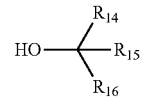

(22)

wherein $R_{14}$ to $R_{16}$ are as defined in general formula (20)

[Formula 28]

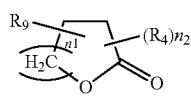

(9)

wherein $R_4$, $n_1$ and $n_2$ are as defined in general formula (2), and $R_9$ is a hydroxyl group

[Formula 29]

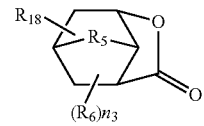

(10)

wherein $R_5$, $R_6$ and $n_3$ are as defined in general formula (3), and $R_{10}$ is a hydroxyl group.

13. A (meth)acrylic copolymer comprising a repeating unit represented by general formula (29), which is obtainable by polymerization of the (meth)acrylate compound according to claim 1:

[Formula 30]

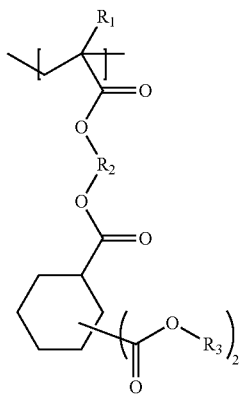

(29)

wherein $R_1$ and $R_2$ are as defined in general formula (1) shown above, and $R_3$ is represented by general formula (2) or (3) shown above and is represented by general formula (20) shown above.

14. The (meth)acrylic copolymer according to claim 13, which further comprises at least one member selected from general formula (31) as a repeating unit, in addition to the repeating unit of general formula (29):

[Formula 31]

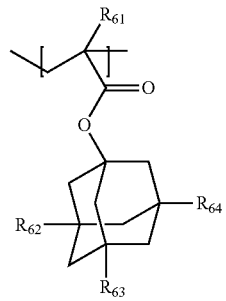

(31)

wherein $R_{61}$ represents a hydrogen atom or a methyl group, $R_{62}$ to $R_{64}$, which may be the same or different, each independently represent a hydrogen atom, a hydroxyl group, a methyl group or an ethyl group.

15. A photosensitive resin composition, which comprises the (meth)acrylic copolymer according to claim 4 and a photoacid generator.

16. A photosensitive resin composition, which comprises the (meth)acrylic copolymer according to claim 5 and a photoacid generator.

17. A photosensitive resin composition, which comprises the (meth)acrylic copolymer according to claim 9 and a photoacid generator.

18. A photosensitive resin composition, which comprises the (meth)acrylic copolymer according to claim 10 and a photoacid generator.

19. A photosensitive resin composition, which comprises the (meth)acrylic copolymer according to claim 13 and a photoacid generator.

20. A photosensitive resin composition, which comprises the (meth)acrylic copolymer according to claim 14 and a photoacid generator.

* * * * *